(12) United States Patent
Murdeshwar et al.

(10) Patent No.: US 12,036,418 B2
(45) Date of Patent: Jul. 16, 2024

(54) SURGICAL DEVICES FOR TREATING BODY TISSUE AND DIAGNOSING PATIENTS

(71) Applicant: GYRUS ACMI, INC., Southborough, MA (US)

(72) Inventors: Nikhil M. Murdeshwar, Maple Grove, MN (US); Thomas J. Holman, Princeton, MN (US)

(73) Assignee: Gyrus ACMI, Inc., Westborough, MA (US)

(*) Notice: Subject to any disclaimer, the term of this patent is extended or adjusted under 35 U.S.C. 154(b) by 168 days.

(21) Appl. No.: 17/136,375

(22) Filed: Dec. 29, 2020

(65) Prior Publication Data
US 2021/0196974 A1 Jul. 1, 2021

Related U.S. Application Data

(60) Provisional application No. 62/955,721, filed on Dec. 31, 2019.

(51) Int. Cl.
*A61N 5/06* (2006.01)

(52) U.S. Cl.
CPC .... *A61N 5/0603* (2013.01); *A61N 2005/0632* (2013.01); *A61N 2005/0635* (2013.01); *A61N 2005/0654* (2013.01); *A61N 2005/0661* (2013.01)

(58) Field of Classification Search
CPC .......... A61N 5/0603; A61N 5/0601; A61N 2005/0632; A61N 2005/0635; A61N 2005/0654; A61N 2005/0661; A61N 2005/061; A61B 1/0676
See application file for complete search history.

(56) References Cited

U.S. PATENT DOCUMENTS

| 5,632,767 | A | * | 5/1997 | Sinofsky | A61N 5/0601 606/7 |
| 6,986,764 | B2 | * | 1/2006 | Davenport | A61B 18/22 606/2 |
| 8,109,981 | B2 | | 2/2012 | Gertner et al. | |
| 2003/0191459 | A1 | | 10/2003 | Ganz et al. | |
| 2004/0204747 | A1 | | 10/2004 | Kemeny et al. | |
| 2006/0167531 | A1 | * | 7/2006 | Gertner | A61N 5/0603 607/86 |

(Continued)

FOREIGN PATENT DOCUMENTS

CN 113116277 A 7/2021

OTHER PUBLICATIONS

Kubodera et al. "A vacuum ultraviolet flash lamp with extremely broadened emission spectra" Appl Phys. Lett. 69 (4), Jul. 22, 1996 (Year: 1996).*

(Continued)

*Primary Examiner* — Lynsey C Eiseman
(74) *Attorney, Agent, or Firm* — Schwegman Lundberg & Woessner, P.A.

(57) ABSTRACT

A surgical device such as a therapy device that can allow a surgeon to treat a target tissue with ultra-violet (UV) light ablation therapy. In one example, the therapy device is configured to treat menorrhagia. In that instance, the therapy device may be configured to effect or destroy the endometrium during a procedure treating menorrhagia.

19 Claims, 12 Drawing Sheets

(56) References Cited

U.S. PATENT DOCUMENTS

| | | |
|---|---|---|
| 2008/0245371 A1 | 10/2008 | Gruber |
| 2008/0249534 A1* | 10/2008 | Gruber ................ A61B 1/0615 |
| | | 606/198 |
| 2011/0301584 A1* | 12/2011 | Beck ..................... A61B 18/22 |
| | | 606/15 |
| 2016/0038621 A1 | 2/2016 | Victor et al. |
| 2018/0104368 A1 | 4/2018 | Dobrinsky et al. |
| 2019/0070432 A1 | 3/2019 | Hill et al. |
| 2019/0275346 A1 | 9/2019 | Maeda |

OTHER PUBLICATIONS

"European Application Serial No. 20217770.5, Response Filed Jan. 7, 2022 to Extended European Search Report dated May 11, 2021", 8 pgs.

"European Application Serial No. 20217770.5, Extended European Search Report dated May 11, 2021", 8 pgs.

\* cited by examiner

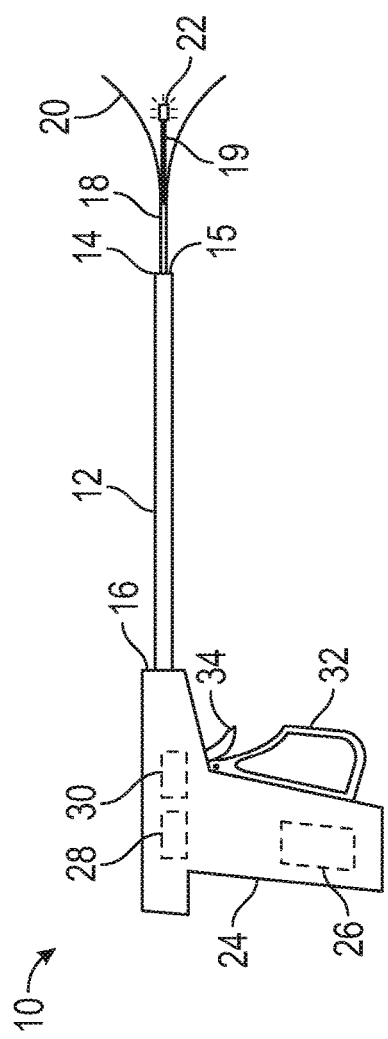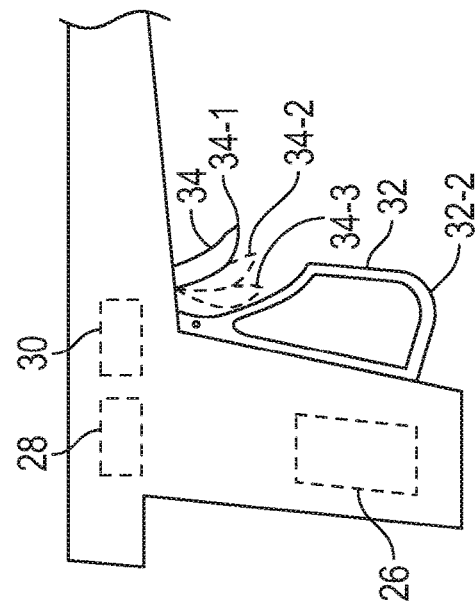
FIG. 1A
FIG. 1B
FIG. 1C

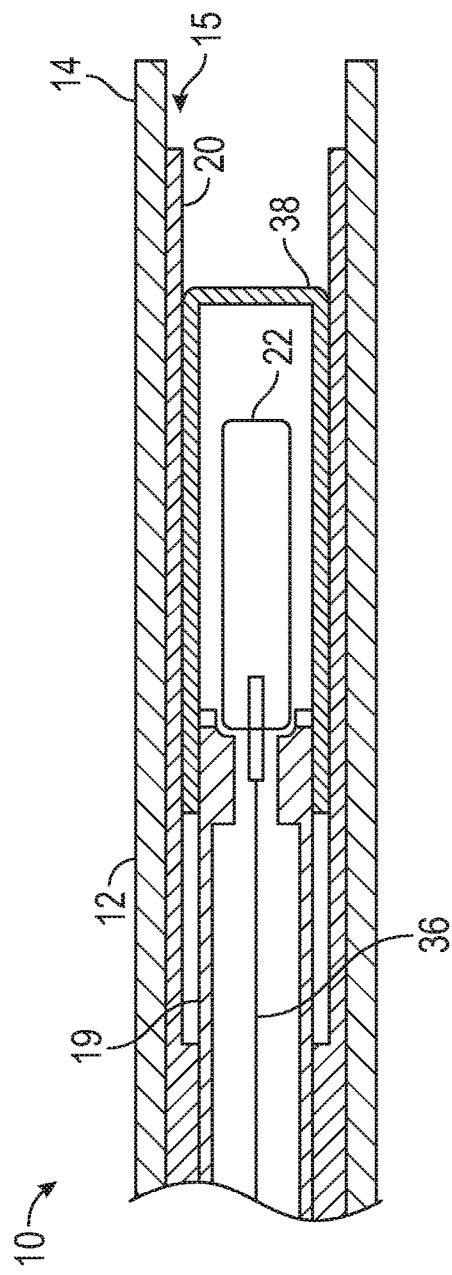
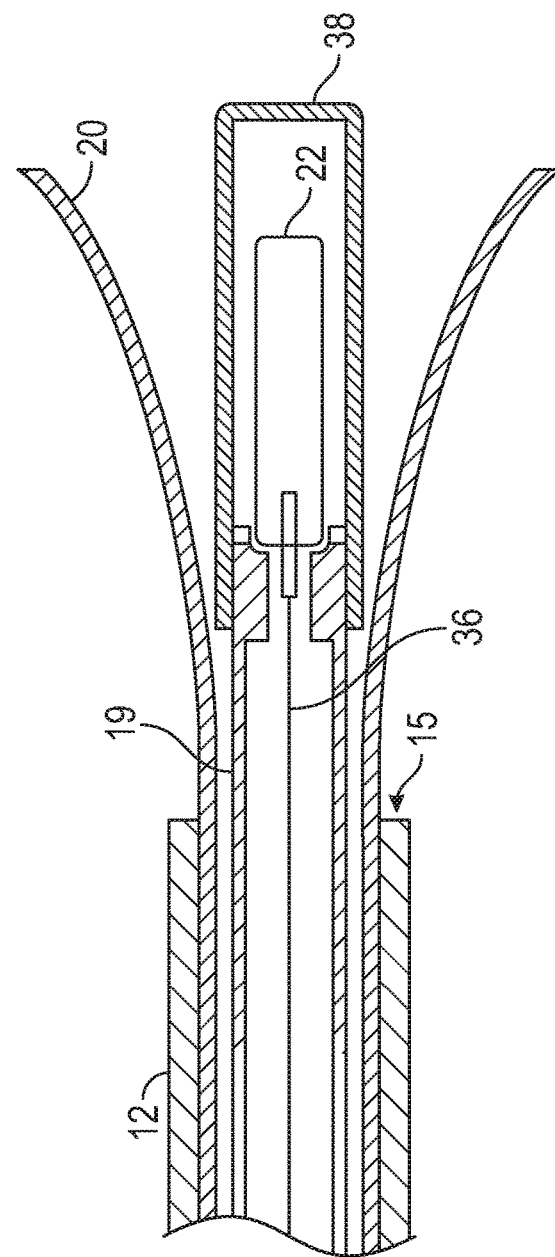

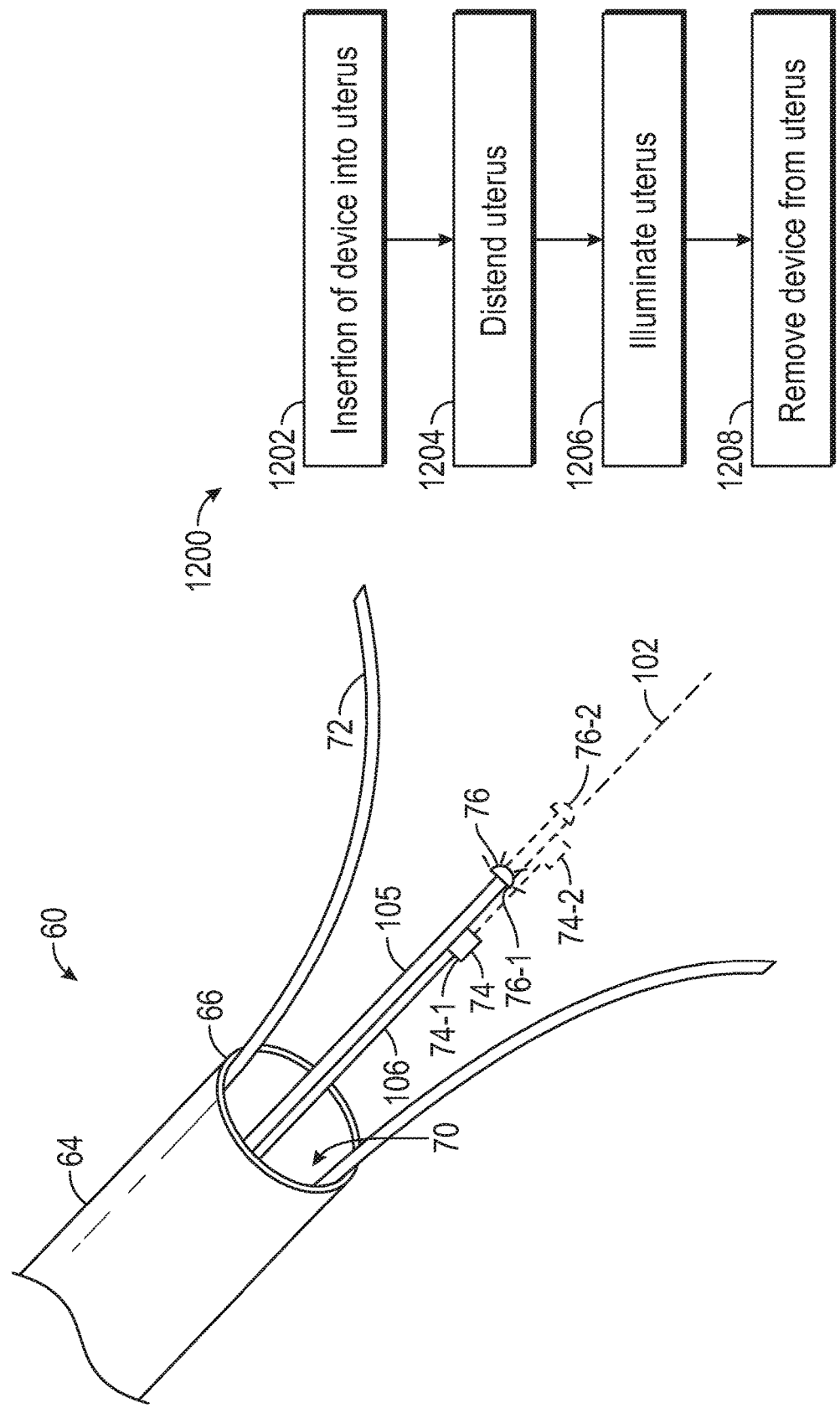

SURGICAL DEVICES FOR TREATING BODY TISSUE AND DIAGNOSING PATIENTS

PRIORITY CLAIM

This application claims priority to U.S. Ser. No. 62/955,721, filed on Dec. 31, 2019, entitled "SURGICAL DEVICES FOR TREATING BODY TISSUE AND DIAGNOSING PATIENTS", the disclosure of which is incorporated by reference in its entirety.

TECHNICAL FIELD

This document pertains generally, but not by way of limitation, to surgical devices, and more particularly, devices used for diagnosing patients and devices for treating body tissue.

BACKGROUND

Menorrhagia is a medical condition defined as abnormally heavy and prolonged menstrual bleeding and pain. In particular, menorrhagia refers to menstrual bleeding lasting more than seven days at a time, and can often include heavy bleeding. Menorrhagia affects more than ten million American women every year, meaning about one out of every five women nationally has menorrhagia. Untreated menorrhagia can cause anemia, a common blood problem in which the patient lacks sufficient healthy red blood cells to carry adequate oxygen throughout the body.

Menorrhagia can be caused by uterine problems, hormonal problems, or other illnesses. Some particular causes can include, but are not limited to, growths or tumors in the uterus, cancer of the uterus or cervix, pregnancy-related problems such as miscarriage or ectopic pregnancy, bleeding disorders, some types of birth control, kidney, thyroid, or liver diseases, infection of the female reproduction organs such as pelvic inflammatory disease, menopause, child birth, fibroids or polyps in the lining or muscles of the uterus, taking certain drugs such as aspirin, or combinations thereof.

OVERVIEW

A variety of approaches can be taken for treatment of menorrhagia. For decades, hormone pills or hysterectomy were used to treat menorrhagia. Recently, surgeons began using various ablation devices to treat menorrhagia by exposing the endometrium to various energy sources, which typically leads to a decrease in menstrual period bleeding and pain. Such treatment can be referred to as global endometrial ablation (GEA). GEA approaches can use a variety of ablation technologies to ablate the endometrium and prevent menorrhagia. Some of these approaches can include radiofrequency (RF) energy, microwave energy, cryogenics, thermal energy, steam, and plasma ablation technologies.

However, some currently available ablation devices have various shortcomings. For example, some ablation devices require the surgeon to manipulate or move the shaft from side to side and/or rotate the shaft inside the uterus to expose the endometrium to the energy source, which can be cumbersome for the surgeon and painful for the patient. Approaches using material (e.g., steam, cryogenics), requires additional means to reduce the risk of leaking the material to areas other than the endometrial tissue.

Some ablation devices require a large outer shaft diameter to accommodate large current carrying conductors. As can be imagined, a large shaft diameter can be painful to insert into a patient and may lead to cervical trauma. Since the shaft diameter requires painful dilation of the patient's cervix, the procedure is done an as in-patient procedure requiring hospital admission and anesthesia. Additionally, some ablation devices are cumbersome to operate. For example, while some ablation devices are intended for single-handed operation, some devices require plugs to seal the uterus during treatment, which necessitates using a second hand. Furthermore, some ablation devices require various mediums (e.g., gas, steam, liquids) that require additional equipment and ports or channels to accommodate the mediums, which can be cumbersome and increase the complexity and cost of the overall procedure.

To help increase efficacy, reduce complications, and increase ease of the procedure, the present disclosure, among other things, describes a therapy device for treating intra-uterine tissue. The therapy device includes an ultra-violet (UV) light transparent distention member translatable within the cannulated shaft configured to distend a patient's uterus and a UV light source configured extend from the distal opening and apply an energy to an intra-uterine tissue sufficient to ablate the uterine tissue.

This disclosure also describes a method of treating menorrhagia in a patient. The method can include introducing a portion of a therapy device into a body cavity of a patient, distending the body cavity by extending the UV light transparent distention member from a cannulated shaft to distend the body cavity, and treating the body cavity by illuminating the body cavity with UV light generated from the UV light source.

Additionally, prior to the treatment of various gynecological conditions, the condition needs to be diagnosed. Gynecologists use hysteroscopy to diagnosis various issues and recommend various treatment options to patients. In hysteroscopy, an endoscope is inserted into the uterus e.g. for inspecting the lining. For the practitioner, the field of diagnostic imaging, for example hysteroscopy, has allowed viewing of the internal lining in uterus with minimal complication and pain. Such imaging tools have been used in different forms for detailed different kinds of inspection.

In the medical field, the large amount of permanently or semi-permanently installed equipment/devices is challenging. The costs for purchasing and costs for maintenance of the equipment, and the complexity necessitate skills and training for the staff.

Additionally, the technical equipment takes up space, they require fixed power supply, and/or supply of fluids etc., and they may be impossible to move close to the practitioner during surgery and therefore they may sometimes be in the way for the staff and they can be difficult to use. Further, a lot of the diagnosing is done as an in-hospital procedure, where a patient is admitted to the hospital because of the equipment needed is generally at the hospital and because the procedure can involve some form of sedations or anesthesia. Patient's may be hesitant to receive the diagnostic hysteroscopy as insurance coverage is unknown and the cost and time associated with an in-hospital procedure.

Sterility and re-useability are closely related. The equipment/devices of an operating room must typically be clean or even sterile before they can be used. Sterility can be accomplished by using a device only once, but typically, the large electrical fixtures including endoscopes and monitors of an operating room are much too expensive to be used only once.

The existing endoscopes are typically two-unit devices made of a relatively inexpensive scope with a camera or with fiber optics, and a very expensive control unit forming part of the fixture of an operating room. The scope and control unit are connected by use of cables, e.g. including optical cables. The existing endoscopes are complicated to use and require adaption of settings between the scope and the control unit. Additionally, sterility can be compromised when the non-sterile control unit is connected to the sterile scope by cables.

To help provide an easily accessible diagnostic tool that can be readily used to help diagnose a patient is provided. The diagnostic tool can be used as an outpatient procedure done in the doctor's office since no large equipment or complex electrical fixtures are needed. This enables not only patients who have access to health providers but also those who do not have access to heal providers. For example, patients can obtain a quick and easy diagnostic in, e.g., a doctor's office, before having to undergo a more complex treatment. This will encourage more women to get diagnosis if they can have the diagnostic procedure done in-office that more doctors can have available since the cost of the device/equipment is minimal. Additionally, in underdeveloped countries, doctors will be able to perform sterile procedures to diagnosis patients that otherwise would not have been diagnosed because the complex diagnostic tools currently used were unavailable.

The present disclosure, among other things, describes a device for visualizing internal tissue of a body cavity that includes a cannulated shaft extending from a proximal end to a distal end, the distal end having a distal opening, a distention member translatable within the cannulated shaft configured to distend the body cavity, a light source configured extend from the distal opening and illuminate the internal tissue of the body cavity, and an image visualization structure configured to visualize the internal tissue of the body cavity to a user.

This disclosure also describes a method of visualizing internal tissue of a body cavity that includes introducing a portion of a device into a body cavity of a patient, distending the body cavity by extending a distention member from the distal opening to distend the body cavity; and illuminating the body cavity with light generated from the light source.

The devices and methods for visualizing internal tissue provide a device with a small overall diameter (e.g., less than 6 mm) such that the diagnosing can occur as an out-patient procedure and can be single-use. That is, either the entire device can be single-use or the shaft can be single use such that after using the device, the shaft can disengage the handle and another shaft can be coupled to the handle.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 1A illustrates a side-view of a therapy device, according to an example of the present disclosure.

FIG. 1B illustrates a portion of the therapy device shown in FIG. 1A.

FIG. 1C illustrates the portion of the therapy device shown in FIG. 1B.

FIG. 2 illustrates a cross-sectional view of a distal end of the therapy device, according to an example of the present disclosure.

FIG. 3 illustrates a cross-sectional view of the distal end of the therapy device shown in FIG. 2.

FIG. 11 illustrates a portion of another device for visualizing internal tissue of the body cavity, according to one example of the present disclosure.

FIG. 12 illustrates a flow chart depicting an example of a method of treating a patient condition such as menorrhagia.

DETAILED DESCRIPTION

Figure 4:
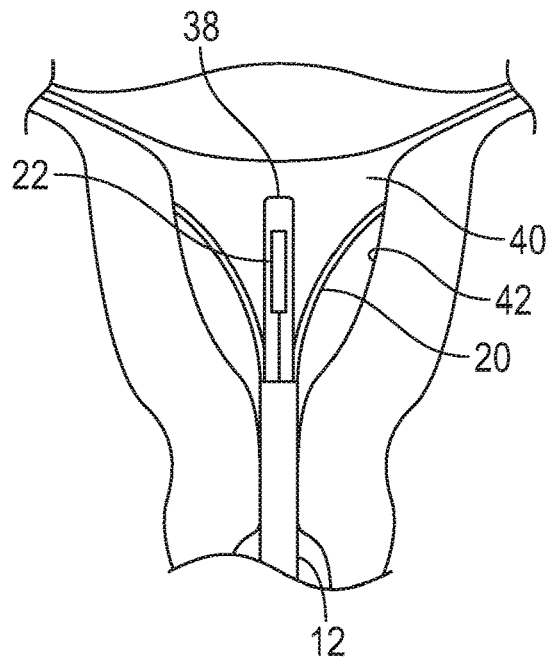
FIG. 4 illustrates a cross-sectional view of a body cavity and a portion of the therapy device located inside the body cavity, according to an example of the present disclosure.

The present disclosure is directed to a surgical device such as a therapy device that can allow a surgeon to treat a target tissue with ablation therapy. The therapy device may be used to treat various target tissues, such as a vessel, tissue, vein, artery, a body cavity such as a uterus, a tumor, the like, or a combination thereof. In one example, the therapy device is configured to treat menorrhagia. In that instance, the therapy device may be configured to effect or destroy the endometrium during a procedure treating menorrhagia.

While the device disclosed in this application may be used to treat menorrhagia, it is understood that the device can be used in other applications as well. For example, the device can be used to treat tissue in the bladder, vagina, esophagus, trachea, urethra, ureter, prostate gland, kidney, intestinal growths or abnormal tissues of the intestine, cancerous tissue, etc.

Using the therapy device according to these teachings to effect a target tissue may mean treating the target tissue by ablating, vaporizing, or otherwise removing tissue. Effecting or treating may mean that the tissue or anatomical feature is destroyed, coagulated, and/or denatured.

The therapy device may be a global endometrial ablation (GEA) device. The therapy device may be an ablation device. The therapy device may comprise one or more energy sources. The therapy device may have the UV light source (e.g., energy source) in electrical communication with one or more power sources. The power source may function to produce, supply, and/or transmit power to the UV light source, via one or more conductors or wires, such that the UV light source can generate or produce an energy that is capable of treating the target tissue. The power source may be part of the therapy device, for example, contained within the handle. The power source may be a discrete component that is electrically connected to the UV light source with one or more electrical conductors or wires. The power source may be an AC energy source, a DC energy source, or both. The energy source may be a battery.

The UV light source may be selected from either UV-A, UV-B, or UV-C lights and be within a UV light wavelength of 100 nanometers (nm) to 400 nm. The UV light source can be selected based on the condition or disease of the patient. UV light source can generate, among other things, heat that can treat (e.g., ablate) that target tissue. The wavelengths or wavelengths of light to be used to treat the patient are selected based on the wavelength or wavelength that will best treat the condition or disease of the patient.

The therapy device can include a UV transparent distension member that has a non-expanded position and an expanded position. The UV transparent distension member can extend from a distal opening of the cannulated shaft of the therapy device to distend a body cavity such as the uterus. The UV light transparent distension member can be formed from a suitable biocompatible and distensible materials. For example, the UV light transparent distension member may be formed from silicone, PET, polyurethane, rubber, or the like. The UV light transparent distension member may be substantially clear or transparent so that the UV light transparent distension member does not interfere with the UV light that is dispersed from the UV light source and the UV light transparent distension member is not damaged by the energy generated by the UV light source.

As discussed herein, the therapy device disclosed is able to be provide an efficient treatment of a target tissue such that the treatment (e.g., ablation) can be provided to a patient with minimal equipment, while minimizing the manipulation or movement required during the treatment. For example, compared to ablation devices that require an energy source to be in contact with the target tissue, the present disclosure can provide the energy source to the target tissue without being in direct contact with the energy source. Moreover, the present disclosure does not us additional materials (e.g., steam or gas) that requires either plugs, pumps, or containment devices to prevent the material from leaking to other areas other than the endometrial tissue.

FIG. 1A illustrates a side-view of a therapy device 10 (also referred to herein as "device 10") with a portion sized and shaped for insertion into a patient, e.g., a uterus of a patient. FIGS. 1B and 1C illustrate a portion of the therapy device 10 shown in FIG. 1A. The device 10 can include a cannulated shaft 12, a UV light transparent distension member 20, a UV light source 22, and a hand piece 24. The device 10 can include, for example, a therapy device for producing one or more intra-uterine tissue effects, such as ablation of endometrial tissue with an in vivo generated energy.

The device 10 can include one or more portions, such as the cannulated shaft 12 (also referred to herein as "shaft 12"), that can be sized, shaped, arranged, or otherwise configured to allow insertion into a patient, such as through an incision in the abdomen or via a transcervical route into the uterus. The shaft 12 can extend from a proximal end 14 to a distal end 16. The device 10 can include a hand piece, such as the handle 24, connected to the proximal end 16 of the cannulated shaft 12. The handle 24 can remain external to the patient and accessible to the physician or other user when a portion of the shaft 12 is inserted into the patient.

The shaft 12 may function to permit a portion of the device to be inserted into a patient or the anatomy, while a portion of the device remains outside of the patient or anatomy. The shaft 12 may be a tubular member. The shaft 12 may be an elongated member that extends along a longitudinal axis. The proximal end 16 of the shaft 12 may be connected to the handle 24. The distal end 14 of the shaft 12 may define a distal opening 15 through which the UV light transparent distention member 20 and the UV light source 22 extend. The shaft 12 may have a relatively small diameter. For example, the diameter of the shaft 12 may be on the order 6 mm or less. Such relatively small sized shaft 12 may function to minimize patient trauma during insertion and/or removal of the shaft 12 into and from the body cavity thus allowing the procedure to be done as an outpatient procedure not requiring hospital admission and anesthesia.

The shaft 12 may be at least partially hollow and may define therein an inner portion. The hollow or inner portion of the shaft 12 is sufficiently sized so that the UV light transparent distension member 20, the UV light source 22, or other instruments, such as a camera, can reside and/or be moved inside or relative to the shaft 12.

The shaft 12 may be substantially straight, may include one or more angles, bends or arcs, or a combination thereof. The shaft 12 may be substantially rigid, substantially flexible, substantially resilient, or a combination thereof.

The device 10 can include an energy source, e.g., a UV light source 22. The UV light source 22 is positioned within the shaft 12 and configured to extend from the shaft 12 during use. For example, the UV light source 22 can move relative to the shaft 12 and the hand piece 24. The UV light source 22 is electrically connected to a power source 26 via one or more electrical conductors. Additionally, the UV light source 22 can be located at a distal end of a shaft 19 that can translate force to move the UV light source 22 relative to the shaft 12 and the hand piece 24 during use. In one example, the UV light source 22 can move relative to the UV light transparent distension member 20.

The UV light source 22 can be coupled to the power source 26. While shown as included within the hand piece 24, the power supply 26 can be external to the hand piece 26. In one example, the power supply 26 can be a battery or can be a power cord that is plugged directly into an AC outlet and/or utilize a DC converter.

The device 10 can include the UV light transparent distention member 20, which can be configured to extend from the distal opening 15 of the cannulated shaft 12 and expand a body cavity such that the energy generated from the light source 22 can be efficiently applied to the target tissue. For example, the UV light transparent distension member 20 can move relative to the shaft 12 and the hand piece 24. For example, the UV light transparent distention member 20 can be located at a distal end of shaft IS that can translate force to move the UV light transparent distention member 20 relative to the shaft 12 and the hand piece 24 during use. In some example, the UV light transparent distention member 20 can move relative to the UV light source 22.

As shown in FIG. 1A, the UV light transparent distention member 20 is at an expanded position. As discussed herein, once the body cavity is distended, the UV light source 22 can be advanced to extend from the distal end 14 of the cannulated shaft to apply the generated energy. As discussed as the UV light source 22 advancing after the body cavity is distended, it also contemplated that the UV light source 22 and the UV light transparent distention member 20 can move simultaneously. That is, a user can actuate the device 10 such that the UV light source 22 and the UV light transparent distention member 20 extend out of the distal opening 15 together at the same time.

As shown in FIGS. 2-4, the UV light transparent distention member 20 can include elongate members having a compressed state when located within the shaft 12 and an expanded or partially expanded state when extending past the distal end 14. While shown for simplicity, the UV light transparent distention member 20 includes two discrete elongated arms. However, more elongated arms are contemplated. Additionally, other structures to distend the body cavity are contemplated.

Referring to FIGS. 1A-1C, the device 10 can include or more user controls 32, 34 for operating and/or controlling the device 10. The one or more user controls 32, 34 may be one or more switches, levers, buttons, triggers, knobs, rotation wheels, or a combination thereof. Manipulation of the one or more user controls may function to extend or retract the UV light transparent distention member 20 relative to the shaft 12 and/or the hand piece 24 and/or the UV light source 22, extend or retract the UV light source 22 relative to the shaft 12 and/or the hand piece 24, and/or the UV light transparent distention member 20, apply or cease applying or change an energy intensity of the UV light source 22, or a combination thereof. The one or more user controls may also be a foot pedal in communication with the therapy device 10, the UV light source 22, the UV light transparent distention member 20, the power source 26, or a combination thereof.

In one example, inside the hand piece 24, the therapy device 10 can include a mechanism 28 coupled to control 32 for moving the UV light transparent distention member 20. Additionally, the therapy device 10 can include a mechanism 30 coupled to control 34 for moving the UV light source 22. As shown in FIGS. 1B and 1C, the control 32 (e.g., a handle) can be actuated by a user to move the control 32 from an initial shown 32-1 in FIG. 1B to a first position 32-2 shown in FIG. 1C. In actuating control 32, mechanism 28 is activated and the UV light transparent distention member 20 can advance from the distal end 14 through the distal opening 15 and move between a non-expanded position shown (shown in FIG. 3 as a compressed state) to an expanded position (shown in FIG. 4 in an expanded state).

As seen in FIG. 1C, the control 34 can include an initial position 34-1, a first position 34-2, and a second position 34-3. As shown in FIG. 1C, the control 34 (e.g., a trigger) can be actuated by a user to move the control 34 from an initial position 34-1 to a first position 34-2. In actuating control 34, mechanism 30 is activated and the UV light source 22 can advance from the distal end 14 through the distal opening 15. In moving control 34 from the first position 34-2 to the second position 34-3, the power source 26 can provide power to the UV light source 22 such that energy needed to treat the target tissue is generated. The UV light source 22 can be electrically coupled via one or more conductors 36 (shown in FIGS. 2 and 3) to the power source 26 such that moving the control 34 from the first position 34-2 to the second position 34-3 the power source can apply power to the UV light source 22.

FIGS. 2 and 3 illustrate a distal portion of the therapy device 10. FIG. 2 illustrates the UV light source 22 and the UV light transparent distention member 20 within the shaft 12. As shown, the UV light transparent distention member 20 is at the non-expanded (e.g., compressed) position. FIG. 3 illustrates the UV light source 22 and the UV light transparent distention member 20 extending from the distal opening 15 of the shaft 12. As shown, the UV light transparent distention member 20 is at the expanded (e.g., uncompressed) position.

The device 10 can include a UV transparent cover 38 that is coupled to the shaft 19. The UV transparent cover 38 can protect the UV light source 22 and the surrounding anatomy in case of breakage of the UV light source 22. In one example, the UV light source 22 can be a flash lamp, which is a gaseous discharge lamp that produces an output of light of short duration and high intensity. The UV light source 22 should be capable of generating high intensity UV light. Various flash lamps can be used successfully in accordance with the invention. In one example, the flash lamp is a xenon flash lamp. The electrical connection between the power source 26 (shown in FIGS. 1A-1C) and the UV light source 22 can cause the UV light source 22 to generate ablation energy.

In one example, the UV light source 22 can include a cold cathode UV bulb. In an example, the UV light source 22 can be connected to a circuit board. The circuit board can include a controller/software and timing mechanism with commands to turn the UV light source 22 on/off, control the length of treatment time in a given time period, etc.

While examples of a flash lamp or cold cathode UV bulb are provided, other sources of high intensity UV light are contemplated. The UV light can provide energy (e.g., light and/or heat) that when placed in close proximity to the target tissue eliminates the need for lasers and light guides. Laser systems are not ideal since light guides tend to attenuate the UV region of the spectrum and laser systems require very expensive support electronics. Additionally, the distention of the body cavity along with using a UV light source provides a device that can efficiently treat the target tissue with minimal equipment and cost.

The invention can use ordinary flash electronics such as those found in disposable flash-equipped film cameras, and thus the entire power unit may be discarded after use in an economical manner. The present UV light source is capable of generating high intensity light in the UV region. The generated light is applied to various parts of a body for multiple purposes including ablating tissue, heating, cross-linking, activating a drug introduced near the tissue, and/or observing a spectral response of tissue Although the light device of the invention has been described thus far in conjunction with endoscopes, other interventional devices such as guide wires, stents, needles, and trocars may be used to introduce the light device inside a body near tissue to be illuminated, so long as the interventional device has an inside diameter sufficient to accept the light device and has an aperture, a port or a window for transmitting the generated light. The device may be operated by a physician who physically manipulates the device and activates the energy source or remotely controls it under visual guidance and with electronic remote control of the device. In accordance with the invention, the light device may be placed near tissue to be illuminated, such that selected areas of the tissue may receive the ablation energy.

FIG. 4 illustrates a body cavity 40 that is a uterus. During a medical procedure, the shaft 12 is inserted into the body cavity 40. The therapy device 10 may include the UV light transparent distention member 20 and the UV light source 22. After the shaft 12 is inside the body cavity 40, the UV light transparent distention member 20 may move relative to the shaft 12 and UV light source 22 and into the body cavity 40 thereby transitioning from the non-expanded position to an expanded position to distend the body cavity 40. Once the body cavity 40 is distended, the UV light source 22 can be moved relative to the shaft 12 and the UV light transparent distention member 20 and into the body cavity 40. Energy generated from the UV light source 22 can be dispersed from the UV light source 22, through the UV transparent cover 38 and the UV light transparent distention member 20 and onto the walls 40 or tissue lining the body cavity 40, which may be the endometrium of the uterus, to medically effect the walls 40. The UV light source 22 may be any one or more of the UV light sources 22 described herein that is capable of generating sufficient energy to effect the walls 40 or tissue lining the body cavity 40.

Figure 5:
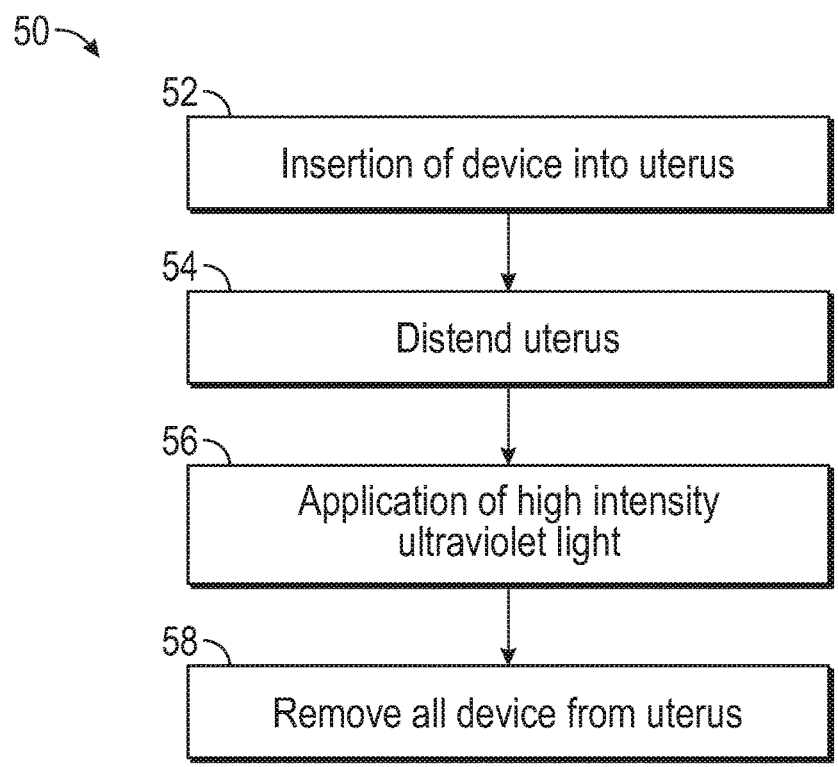
FIG. 5 illustrates a flow chart depicting an example of a method of treating a patient condition such as menorrhagia.

FIG. 5 illustrates a flow chart of method 50 of treating a patient with an ablation device. The method 50 can include inserting the device into the uterus of a patient (52), distending the uterus (54), applying high intensity UV light to the target tissue (56) to ablate the target tissue of the uterine surface, and removing the device form the uterus (58).

First, in step 52, the operator can insert, the device into the patient's uterus. The operator can insert the distal end of the device into the patient in a transcervical manner without other incision or entry point. In this step, the UV light transparent distention member is in a compressed state. The diameter of a cross-section of the distal end of the device entering the patient is less than about 6 mm. This can, for example, allow for more efficient transcervical insertion with less patient pain.

Subsequently, in step 54 the operator can distend the uterus by manipulating one or more user controls such as control 32 (shown in FIGS. 1A-1C), As control 32 is manipulated, the UV light transparent distention member extends from the shaft transitioning from the compressed state to the uncompressed state such that the uterus is distended in preparation of receiving treatment.

In step 56, energy from the UV light source is applied to the surrounding tissue. For example, the control 34 can initially be moved from an initial position to a first position to move the UV light source relative to the shaft and into the distended body cavity. Once in position, the control 34 (or another control) can be manipulated to generate the energy from the UV light source. The generated energy can ablate the target tissue. The application of the generated energy can be done over a single constant, time period or in pulses. The types of UV light sources and target tissue can determine the exact protocol for applying the generated energy and how quickly and efficiently the target tissue is treated. Finally, at step 58, the operator can turn off the device and remove it from the patient.

The proposed device and methods discussed herein allow for delivery of energy generated from a UV light source to ablate endometrial tissue with a lower risk of generating or leaking steam outside the uterus, such as into the vagina, and increase the ease of ablation. Additionally, the device itself is small and less bulky.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

The present inventors realized that a device similar to the device shown in FIGS. 1-4 could also be beneficial for diagnosing various conditions. Thus, FIGS. 6-10 disclose a device for visualizing internal tissue. Because of the minimal equipment and size needed the device can be used to easily diagnose a variety of conditions in a doctor's office enabling a patient to consider various therapy or treatment options before having to undergo a more invasive procedure with a more complex therapy device that may require hospitalization and anesthesia. Additionally, in underdeveloped areas, the visualization device can enable those not able to access clinics and hospitals to have a sterile, safe, and simple procedure to diagnosis a condition that may have gone undetected without access to this visualizing device.

It is an object of the invention to improve sterility, safety of operation, and simplicity of devices for hysteroscopy and to reduce the risk of having wrong settings, bad connectivity, or lack of compatibility between releasably connected units of a device. It is a further object to ease insertion and to improve hysteroscopy.

In an example, the device is for visualization of internal tissue of a patient's uterus. The device can include a working shaft including a cannulated outer shaft, a distention member, a light source, and an image visualization structure. The device can include a hand piece, e.g., a handle, that is coupled to the working shaft. As discussed herein, the overall device can be single-use such that after one use the device can be discarded. In one example, the working shaft is reversibly coupled to the handle such that the working shaft can be discarded after a single-use and the handle after being sterilized, can be reversibly coupled to another working shaft The handle can be dimensioned to be held by a user's hand and it may include various components such as a power supply, controls, mechanisms and an image display portion. The distention member can be mechanically coupled to a control and mechanism such that when actuated, the distention member extends from the distal opening of the cannulated shaft and transitions from a compressed state to an uncompressed state to distend the body cavity. The light source and the image visualization structure can then be advanced from the distal opening and the light source can be activated to illuminate the body cavity such that the image visualization structure can capture images or video of the body cavity. For example, both the light source and the image visualization structure can be mechanically coupled to a control and a mechanism such that when actuated, the light source and the image visualization structure can advance from the distal opening. The light source can be electrically coupled to a power source that can supply power to illuminate the light source. The image visualization structure can be electrically coupled to a power supply and an image display such that the user can visualize the internal tissue of the body cavity. In one example, image display can be a monitor that can display images or videos captured by the image visualization structure. In one example, the image display can be a connection site that can connect with a discrete display monitor. Further, the image display can be a lens that a user can look through and visualize the internal tissue of the body cavity.

In one example, the image visualization structure is configured to communicate video signals with a monitor, and the cannulated shaft that contains the distention member, the light source, and the image visualization structure is dimensioned for insertion into the patient's uterus through the cervix and has a diameter of less than 6 mm.

Since the handle is dimensioned to be held by a user's hand and since the working shaft is connected to or reversibly connectable to the handle, the handle may be used without connection to any external devices. The device according to the invention therefore becomes easy to use directly upon removal from the package without having to assembly cables or attached external camera or monitor. This reduces the risk of errors, reduces the risk of combining non-compatible items, and reduces the risk of contaminating the device during connection to external components.

In one example, the working shaft is reversibly connected to the handle such that alter one working shaft has been used, it can be detached from the handle and discarded, and the handle can be sterilized and reused with another working shaft. As discussed herein, the inner portion of the cannulated shaft is not in fluid communication with the inner portion of the handle, thus minimizing any potential contamination between patients.

The handle can be independently powered by a battery, and it may be completely fitted with any necessary parts such as a monitor. In that way, the device may form a complete, independent, hysteroscopy device, e.g. suitable for single usage. Again, the overall device (handle and working shaft) can be single use or the working shaft can be single use.

The image visualization structure can be constituted by a lens located at the distal end, and the device may comprise fiber optical cables or other cables, extending from the lens through the elongated conduit to a camera inside the control unit. In one embodiment, the image capturing structure is constituted by a camera located at the distal end, e.g. a camera with an electronic circuit for converting the image into an electrical signal. In this embodiment, the captured images could be transmitted by electrical cables through the elongated conduit to further electronic processing in the control unit. The term "Camera", herein, covers any kind of structure for capturing an image or a series of images, e.g. for making a video sequence. Particularly, the camera may include a CCD, CMOS chip, lens, and other elements known in the art for capturing images.

The device can include a light source that can illuminate the inside of the uterus. For example, the light source can be one or more LEDS. The image visualization structure may particularly be configured to communicate the image in the form of electrical signals in analogue form. This alleviates the need for digital electronics at the distal end of the elongated member and thereby enables a more compact design which is desirable for providing an easier and potentially less painful access through the cervix.

It should be understood that the detailed description and specific examples, while indicating embodiments of the invention, are given by way of illustration only, since various changes and modifications within the spirit and scope of the invention will become apparent to those skilled in the art from this detailed description.

The tissue visualization device comprises an image visualization structure configured to capture picture of a desired tissue. The image visualization structure may be configured for non-electrical capturing or for electrical capturing of pictures. An example of an image capturing structure for non-electrical capturing is a lens by which the picture is transferred through the elongated member to a camera in the handle. An example of an image capturing structure for electrical capturing is a camera, e.g. based on one or more CCDs sensitive in one or more wavelength. The electrically captured picture is transferred by electrical cables through the cannulated shaft to the handle. The pictures could be still pictures and/or video by use of any method and format known per se.

Figure 6:
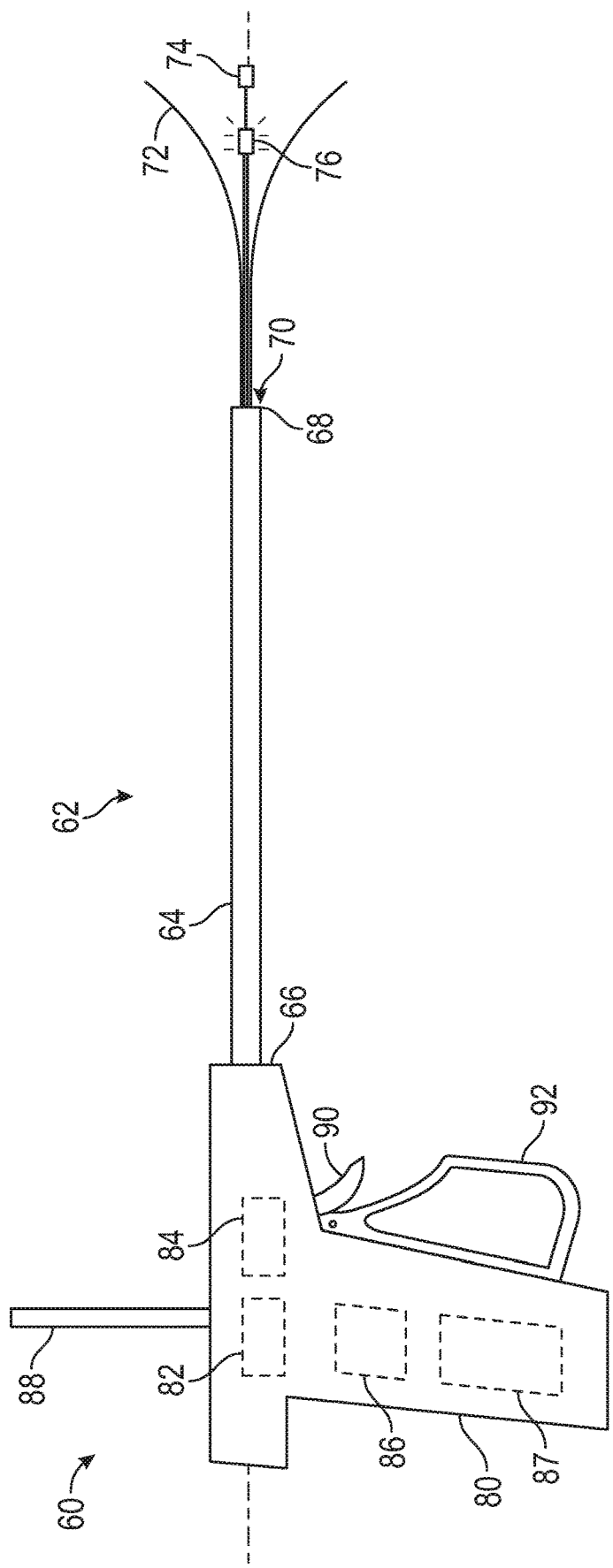
FIG. 6 illustrates a side-view of a device for visualizing internal tissue of a body cavity, according to one example of the present disclosure.

FIG. 6 illustrates the device 60 for visualizing internal tissue of a body cavity, such as a uterus. The device 10 can include a working shaft 62 that is couple to or reversibly coupled to a handle 80. The working shaft 62 can include a cannulated shaft 64, a distension member 72, a light source 76, and an image visualization structure 74. The device 60 is similar to the device 10 described above but device 60 does not include a therapy light source (e.g., UV light source) but a light source 76 solely for illuminating the body cavity. In one example, the distension member 72 can be the same as the UV light transparent distention member 20, however, the distention member 72 can be formed out of any transparent material and not necessarily a UV light transparent material. Additionally, the device 60 can include the image visualization structure 74, which can be incorporated into the device 10. As discussed herein, the device 60 can also include an image display 88, which would be a display monitor to display pictures or videos or could be a lens that a user looks into. Furthermore, the image display 88 could be a connection that can be coupled to an external display monitor.

The device 10 can include one or more portions, such as the cannulated shaft 64 (also referred to herein as "shaft 64"), can be sized, shaped, arranged, or otherwise configured to allow insertion into a patient, such as through an incision in the abdomen or via a transcervical route into the uterus. The shaft 64 can extend from a proximal end 66 to a distal end 68 having a distal opening 70. The device 60 can include a hand piece, such as the handle 80, connected to the proximal end 66 of the cannulated shaft 64. The handle 80 can remain external to the patient and accessible to the physician or other user when a portion of the shaft 64 is inserted into the patient.

The shaft 64 should be made as small as possible for patient comfort. In one example, the diameter of the shaft 64 may be on the order 6 mm or less. This relatively small sized shaft 12 may function to minimize patient trauma during insertion and/or removal of the shaft 12 into and from the body cavity thus allowing the procedure to be done as an outpatient procedure not requiring hospital admission and anesthesia.

The hollow or inner portion of the shaft 12 is sufficiently sized so that the distension member 72, the light source 76, and the image visualization structure 74 can reside and/or be moved inside or relative to the shaft 64.

The light source 76 is positioned within the shaft 64 and configured to extend from the shaft 64 during use. For example, the light source 76 can move relative to the shaft 64 and the hand piece 80. The light source 76 is electrically connected to a power source 87 via one or more electrical conductors. While shown as included within the hand piece 87, the power supply 26 can be external to the hand piece 87. In one example, the power supply 87 can be a battery or can be a power cord that is plugged directly into an AC outlet and/or utilize a DC converter.

The device 60 can include the distention member 72, which can be configured to extend from the distal opening 70 of the cannulated shaft 64 and expand a body cavity such that the light generated from the light source 76 can be efficiently applied to the body cavity. As discussed herein, the distention member 72 can be the same as distention member 20 of device 10.

Similarly, handle 80 can include one or more user controls 90, 92 for operating and/or controlling the device 60. The one or more user controls 90, 92 may be one or more switches, levers, buttons, triggers, knobs, rotation wheels, or a combination thereof. Manipulation of the one or more user controls may function to extend or retract the distention member 72, the light source 76, and the image visualization structure 74. The one or more user controls may also be a foot pedal in communication with the device 60, the light source 76, the distention member 72, the image visualization structure 74, the power source 87, or a combination thereof.

In one example, inside the hand piece 24, the therapy device 10 can include one or more mechanisms 82, 84, 86 coupled to controls 90, 92 for moving the distention member 72, the light source 76, and the image visualization structure 74. For example, in actuating control 92, mechanism 82 is activated and the distention member 72 can advance from the distal end 68 through the distal opening 70 and move between a non-expanded position shown to an expanded position, as discussed in FIGS. 3 and 4.

Figure 7:
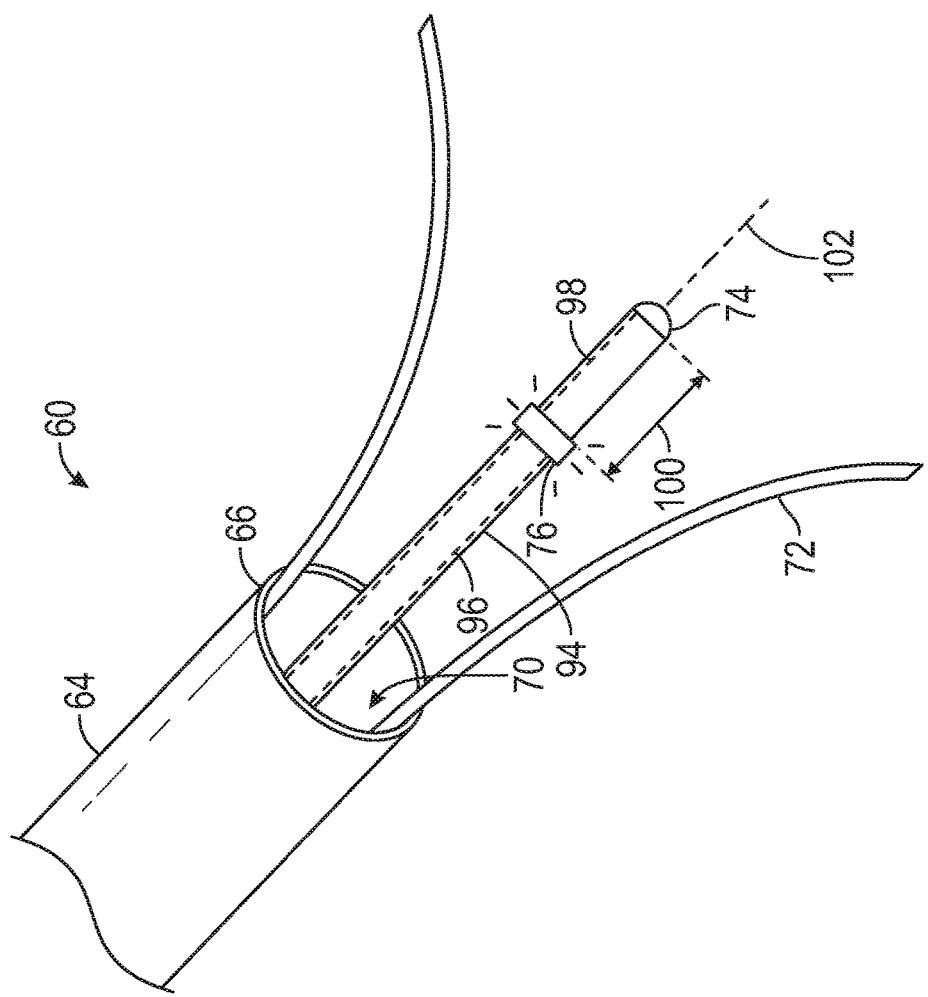
FIG. 7 illustrates a portion of the device shown in FIG. 6.

Additionally, the distention member 74 and the image visualization structure 76 can be mechanically coupled to the same shaft, e.g., shaft 94 shown in FIG. 7. In the example shown in FIG. 7, the image visualization structure 74 is at the distal end of the shaft 94 and the light source 76 is positioned along the shaft 94. Light source 76 is electrically coupled to a power supply via electrical connection 96 and the camera is coupled to the image display 88 (see FIG. 6) via connection 98, which will depend on what type of image visualization structure 74 is used. The distention member 72 in FIG. 7 is shown in an expanded state where the image visualization structure 74 and the light source 76 have been moved through the distal opening. While the light source 76 and the image visualization structure 74 are mounted/coupled to the shaft 94, a space 100 between the two can be maintained. In this example, the space 100 along the longitudinal axis of the cannulated shaft 64 is fixed because both the image visualization structure 74 and the light source 76 are coupled to the same shaft 94. However, in other examples, the space 100 can be changed during use.

Figure 8:
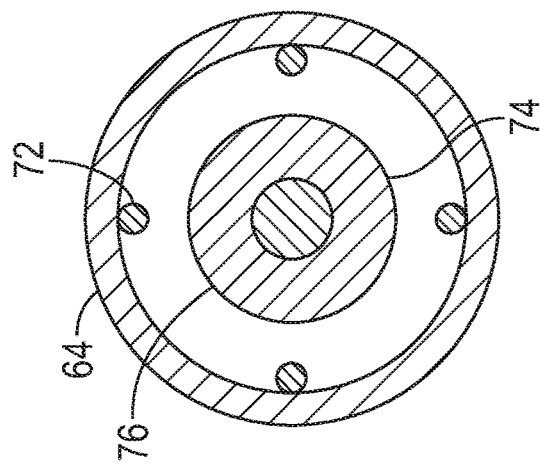
FIG. 8 illustrates a cross-sectional view of a portion of an example device for visualizing internal tissue of a body, according to one example of the present disclosure.

FIG. 8 illustrates a cross-sectional view along the light source 76 when the light source 76 surrounds the image visualization structure 74. That is, there is no longitudinal space between the image visualization structure 74 and the light source 76. As seen in FIG. 8, the distention member 72 includes four elongate arms 72 (while sometimes illustrates as two for simplify).

Figure 10:
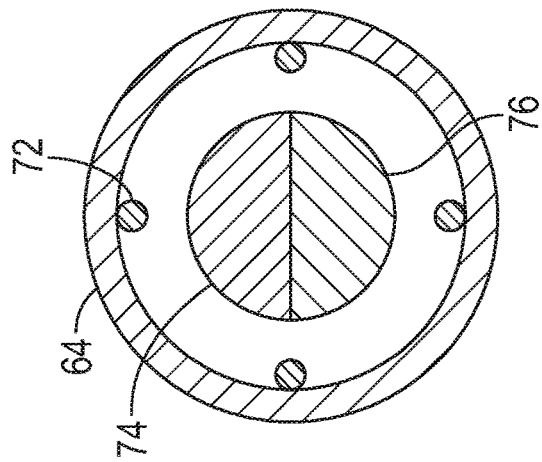
FIG. 10 illustrates a cross-sectional view of a portion of an example device of visualizing internal tissue of the body cavity, according to one example of the present disclosure.
Figure 9:
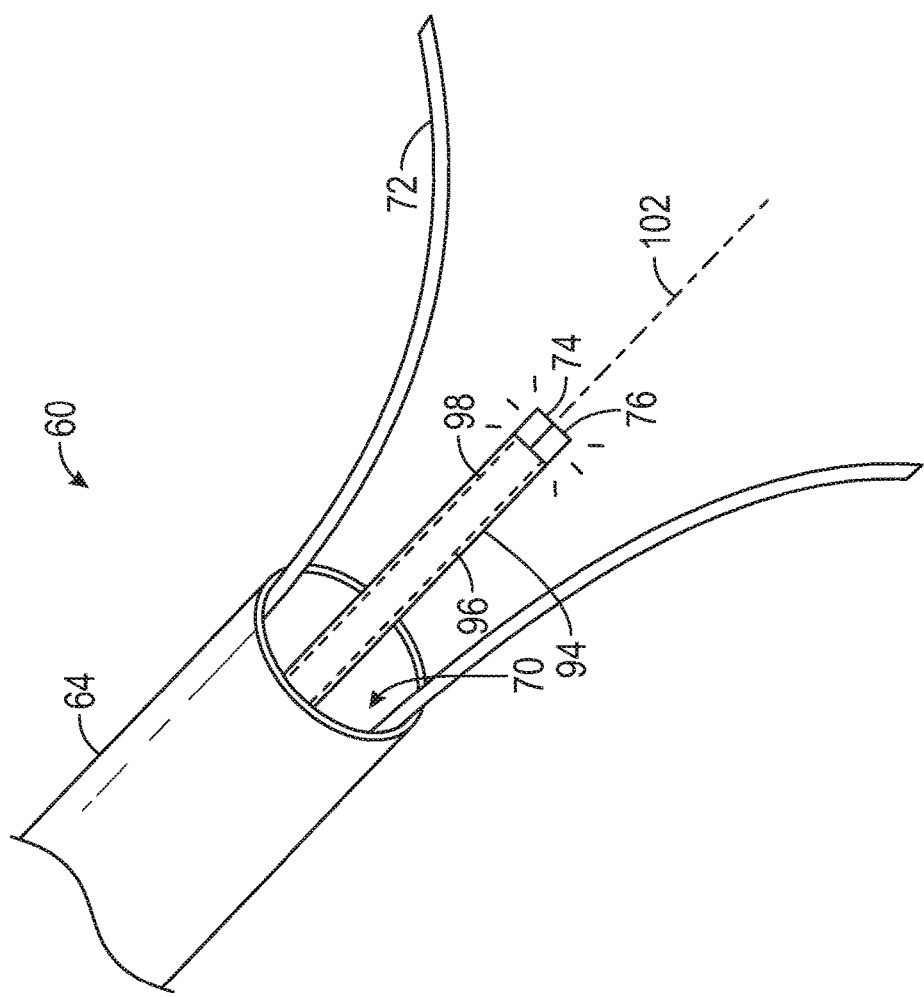
FIG. 9 illustrates a portion of another device for visualizing internal tissue of the body cavity, according to one example of the present disclosure.

FIGS. 9 and 10 illustrate an example of device 60 where the image visualization structure 74 and the light source 76 are both positioned at a distal end of the shaft 94. FIG. 9 illustrates the device 60 in an expanded position and FIG. 10 illustrates a cross-section along the shaft 94 along the light source 76 and the image visualization structure 74 when they are positioned within the cannulated shaft 64.

FIG. 11 illustrate san example of device 60 where the image visualization structure 74 and the light source 76 are coupled to separate distinct shafts 106, 105, respectively, such that the image visualization structure 74 and the light source 76 can move relative to each other. As seen in FIG. 11, the image visualization structure 74 can move from a first position 74-1 to a second position 74-2 and the light source 76 can move from a first position 76-1 to a second position 76-2. In one example, both the longitudinal axis of the light source 76 and the image visualization structure 74 can be offset from the longitudinal axis 102 of the cannulated shaft 64.

FIG. 12 illustrates a flow chart of method 1200 of visualizing internal tissue of a boy cavity. The method 1200 can include inserting the device into the uterus of a patient (1202), distending the uterus (1204), illuminating the body cavity (1206), and removing the device form the uterus (1208).

First, in step 1202, the operator can insert the device into the patient's uterus. The operator can insert the distal end of the device into the patient in a transcervical manner without other incision or entry point. In this step, the distention member is in a compressed state. The diameter of a cross-section of the distal end of the device entering the patient is less than about 6 mm. This can, for example, allow for more efficient transcervical insertion with less patient pain.

Subsequently, in step 1204 the operator can distend the uterus by manipulating one or more user controls. As a control coupled to the distention member is manipulated, the distention member extends from the shaft transitioning from the compressed state to the uncompressed state such that the uterus is distended.

In step 1206, power is supplied to the light source such that the light source can generate light an illuminate the body cavity for visualization. The light source and the image visualization structure can be manipulated to move along the longitudinal axis such that target tissue can be visualized and viewed by a doctor. Once the body cavity is visualized, the doctor can turn off the power to the light source, move the distention member back into the cannulated shaft, and remove the device. The proposed device and methods discussed herein allow for quick, single-use, visualization tool that can be used by a variety of specialist to quickly visualize and diagnosis a condition within a body cavity Referring back to UV ablation, the UV light generation can occur in vivo or external to the patient. Additionally, in various examples, the type of UV light applied can vary. For example, some UV light wavelengths can generate more heat and penetration than other wavelengths. Thus, it can be beneficial to be able to provide a patient with different UV lights during a single ablation treatment. In one example, the endometrium varies between patient to patient and depending on the condition being treated and the specific anatomy, a more effective treatment may occur if different UV lights can be applied to the patient.

Figure 13:
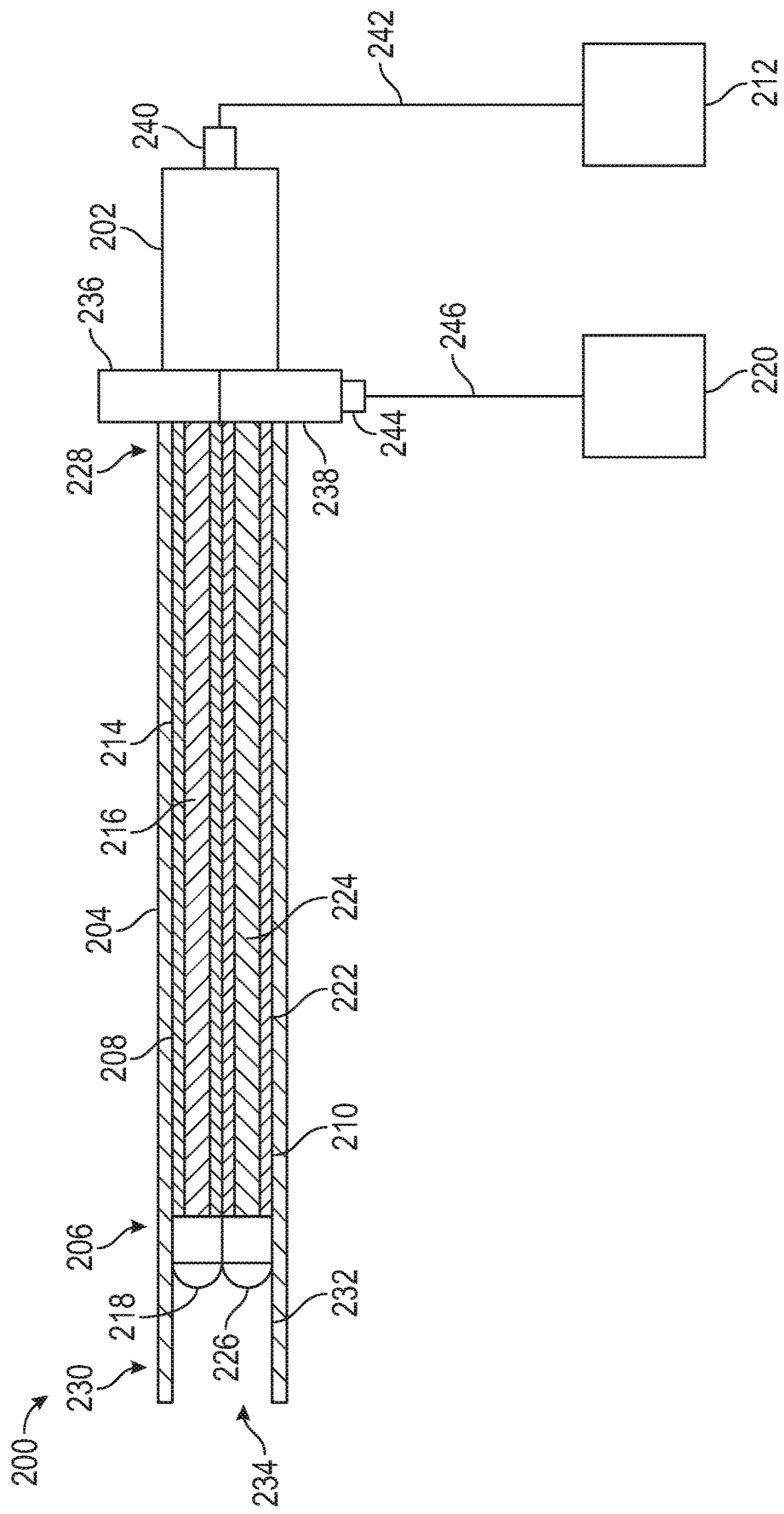
FIG. 13 illustrates a side-view of a therapy device, according to an example of the present disclosure.

FIG. 13 is a schematic illustration of therapy device 200 (also referred to herein as "device 200") that can apply UV light to target tissue. The therapy device 200 generates the UV light outside of the body such that various light sources 212 can be coupled to the therapy device 200 to provide different wavelengths within the UV band to provide ablation to the target tissue.

Therapy device 200 can comprise handle or handpiece 202, outer shaft 204, and surgical instrument 206. The surgical instrument 206 can deliver UV light to the target tissue. The surgical instrument 206 can include a therapy light system 208 and optionally an optical system 210 and/or imaging system. The therapy light system 208 can comprise a light source 212, light delivery shaft 214, light conductor 216, and light emitter 218.

The optical system 210 can include any means such that an operator can view the target tissue. In an example the optical system 210 can comprise a light source 220, light delivery shaft 222, light conductor 224, and tip 226. The optical system 210 and/or imaging system can be used to identify target tissues, immediately measure the treatment of the target tissue to determine if more treatment is needed, and determine if the procedure is complete. One example of such an optical system is disclosed in U.S. Provisional Patent Application 62/940,328, filed Nov. 26, 2019, titled "Surgical devices with Integrated Lighting Systems," which is incorporated by reference in its entirety.

The outer shaft 204 can include an elongate member extending from a proximal portion 228 to a distal portion 230. The outer shaft 204 defines a lumen 232 extending from the proximal portion 228 to the distal portion 230 including a distal opening 234. The handpiece 202 can be mounted or connected to the proximal portion 228 of the outer shaft 204. Portions of the therapy light system 208 and the optical system 210 can run within or along the outer shaft 204, such as from the proximal portion 228 to the distal portion 230.

In examples, the outer shaft 204 can be sized, shaped, or arranged for performing laparoscopic procedures in conjunction with a laparoscope as well as performing transcervical procedures. As such, shaft 204 can be inserted into an incision in the epidermis of a patient, through a body cavity of the patient and into an organ or transcervically into a uterus. Thus, it is desirable for the diameter or cross-sectional shape of shaft 204 to be as small as possible to facilitate minimally invasive surgical procedures and minimal dilation of the cervix. The outer shaft 204 can be rigid and formed from a metal or plastic material. In an example, the outer shaft 204 can have a diameter of less than about 6 mm. The proximal portion 228 can be near an operator when the device 200 is in use.

Handpiece 202 can comprise any device suitable for facilitating manipulation and operation of therapy device 200. Handpiece 202 can be located at the proximal portion 228 or another suitable location along shaft 204. In examples, handpiece 202 can comprise a pistol grip, a knob, a handlebar grip and the like.

Light conductor 216 can comprise a medium for transmitting light from light source 212 to light emitter 218. Light conductor 216 can be located within the light delivery shaft 214 extending from the proximal portion 228 to the light emitter 228 at the distal portion 230. Light conductor 216 can comprise a material suitable for transmitting waves of electromagnetic radiation at various wavelengths and, in particular, wavelengths within the UV band of 100 nm to 400 nm. Light conductor 216 can be coupled to light source 212 via cable 242 and connector 240. Cable 242 can comprise an extension of light conductor 216 and can be fabricated from the same material as light conductor 216. In examples, light conductor 216 and cable 242 can comprise fiber optic cables. In examples, the fiber optic cables can comprise glass and plastic fibers jacketed with one or more protective coatings. Light emitter 218 can be located at or near the distal end of light conductor 216. Light emitter 218 can be coupled to light conductor 216 by any suitable means. In examples, light emitter 218 can comprise a lens for focusing or a diffuser for spreading light waves from light conductor 216. Light emitter 218 can be unidirectional or omnidirectional. Light emitter 218 can comprise a glass or plastic body of transparent material. However, in additional examples, a separate light emitter is not used and light conductor 216 can comprise an end-emitting fiber such that the distal or terminal end of light emitter 218 can comprise light emitter 218.

The optical system 210 can include similar components as the therapy light system 208 but provide a visual light that can be coupled to a camera. Thus, the light conductor 224 can can comprise a medium for transmitting light from light source 220 to light emitter 226. Light conductor 224 can be located within the light delivery shaft 222 extending from the proximal portion 228 to the light emitter 226 at the distal portion 230. Light conductor 224 can comprise a material suitable for transmitting waves of electromagnetic radiation at various wavelengths. Light conductor 224 can be coupled to light source 220 via cable 246 and connector 244. Cable 246 can comprise an extension of light conductor 224 and can be fabricated from the same material as light conductor 224. In examples, light conductor 24 and cable 246 can comprise fiber optic cables. In examples, the fiber optic cables can comprise glass and plastic fibers jacketed with one or more protective coatings. Light emitter 226 can be the same as light emitter 218.

Actuation devices 236, 238 can be attached to handpiece 202 to operate the therapy device 200. Actuation devices 236, 238 can comprise one or more of buttons, triggers, levers, knobs, dials and the like and can comprise any suitable device for allowing operation of therapy device 200 from handpiece 202. In examples, actuation device 236 can be actuated to operate the therapy light system 208 and the actuation device 238 can be actuated to operate the optical system 210 via any type of linkage such as a mechanical linkage, an electronic linkage, an electric linkage, a fluid linkage or an acoustic linkage.

In an example, the light delivery shaft 214 of the therapy light system 208 and the light delivery shaft 222 of the optional system 210 can be coupled such that they cannot move relative to each other. That is, they can be linearly locked together such that they move within the outer shaft 202 together. In another example, the light delivery shaft 214 of the therapy light system 208 and the light delivery shaft 222 of the optional system 210 are not linearly locked and can move relative to one another.

As mentioned, therapy light source 212 can be coupled to therapy light conductor 216 via cable 240. Connector 240 can comprise any suitable device for linking light conductor 216 and cable 242 such that fibers disposed therein can be adjoined in an end-to-end manner. As such, therapy light source 212 can be located remotely from therapy device 200. In examples, light source 212 can comprise a stand-alone module couplable to the therapy device 200 via cable 242. In additional examples, light source 212 can be attached directly to the exterior of handpiece 202 via connector 24 without using cable 242. As such, light source 212 can be removable, thereby allowing for attachment of different light generators that produce different intensities or wavelengths, which, as discussed herein, can allow for application of various types of UV light during a single treatment. In additional examples, light source 212 can be incorporated into handpiece 202 such that connector 240 is not used.

Figure 14:
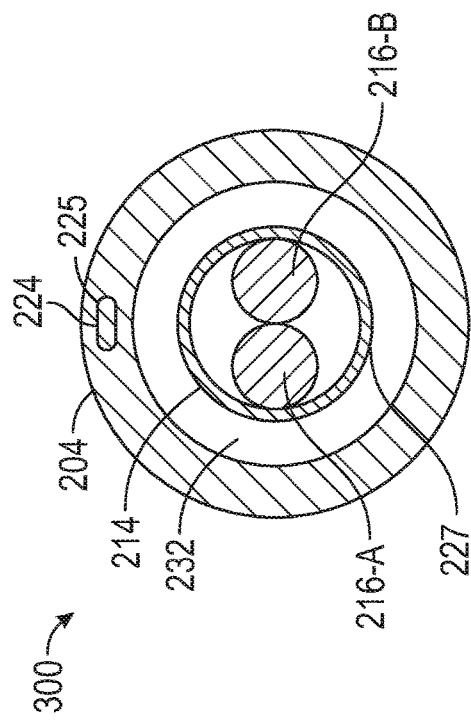
FIG. 14 illustrates a cross-sectional view of a therapy device, according to an example of the present disclosure.

FIG. 14 illustrates an example of a therapy device 300 that can provide more than one type of UV light to a target tissue. FIG. 14 illustrates a cross-sectional view of therapy device 300. Therapy device 300 can be coupled to a handle 20 (seen in FIG. 13). Therapy device 300 can include the outer shaft 204, an optical light system 225 including an optical light conductor 224 and a therapy light system 227 including more than one therapy light conductor, e.g., therapy light conductors 216-A, 216-B. As seen in FIG. 14, the optical system is located within a wall of the outer shaft 204 such that optical light conductor 224 extends along the wall of the outer shaft 224. However, other configurations are contemplated such as the optical light conductor 224 can extend within the lumen 232 of the outer shaft 204 or be included within the therapy light shaft 214 including the therapy light conductors 216-A, 216B.

The therapy light system in FIG. 14 can include more than one therapy light system 227 such as therapy light system 208 as disclosed in FIG. 13. As seen in FIG. 14, the therapy light conductors 216-A, 216-B are both located within the therapy light shaft 214 such as a fiber optic cable. However, therapy light conductors 216-A, 216-B can be separate from each other. Each therapy light conductor can be coupled to a light source that can generate different wavelengths within the UV band. For example, therapy light conductor 216-A can be coupled to a light source configured to generate wavelengths between 100 nm to 200 nm and therapy light conductor 216-B can be coupled to a light source configured to generate wavelengths between 200 nm to 400 nm. Thus, a single therapy device 300 can provide more than one UV light to treat the target tissue. Compared to FIG. 13, the device 300 in FIG. 14 enables an operator to easily activate a different UV light, if needed, during the procedure, without having to detach the first light source and couple a second light source. While shown with two therapy light conductors, more than two therapy light conductors can be included within the therapy device 300.

Figure 15:
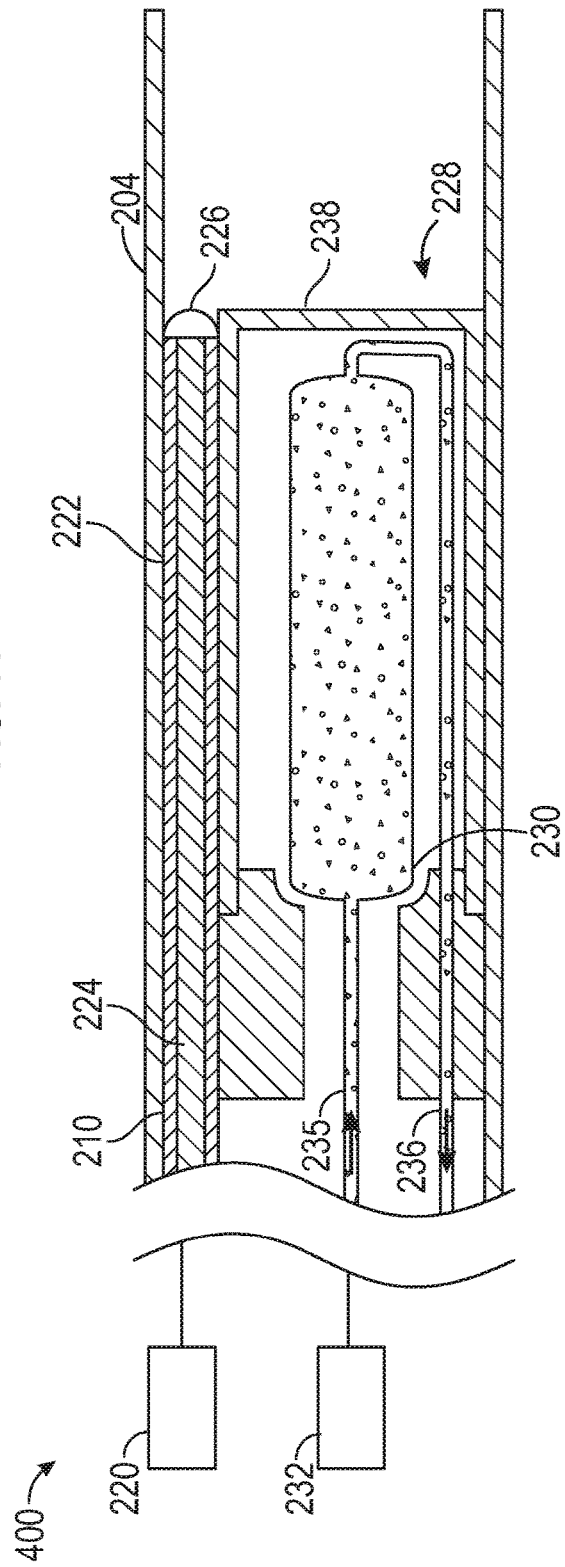
FIG. 15 illustrates a side-view of a portion of a therapy device, according to an example of the present disclosure.
Figure 16:
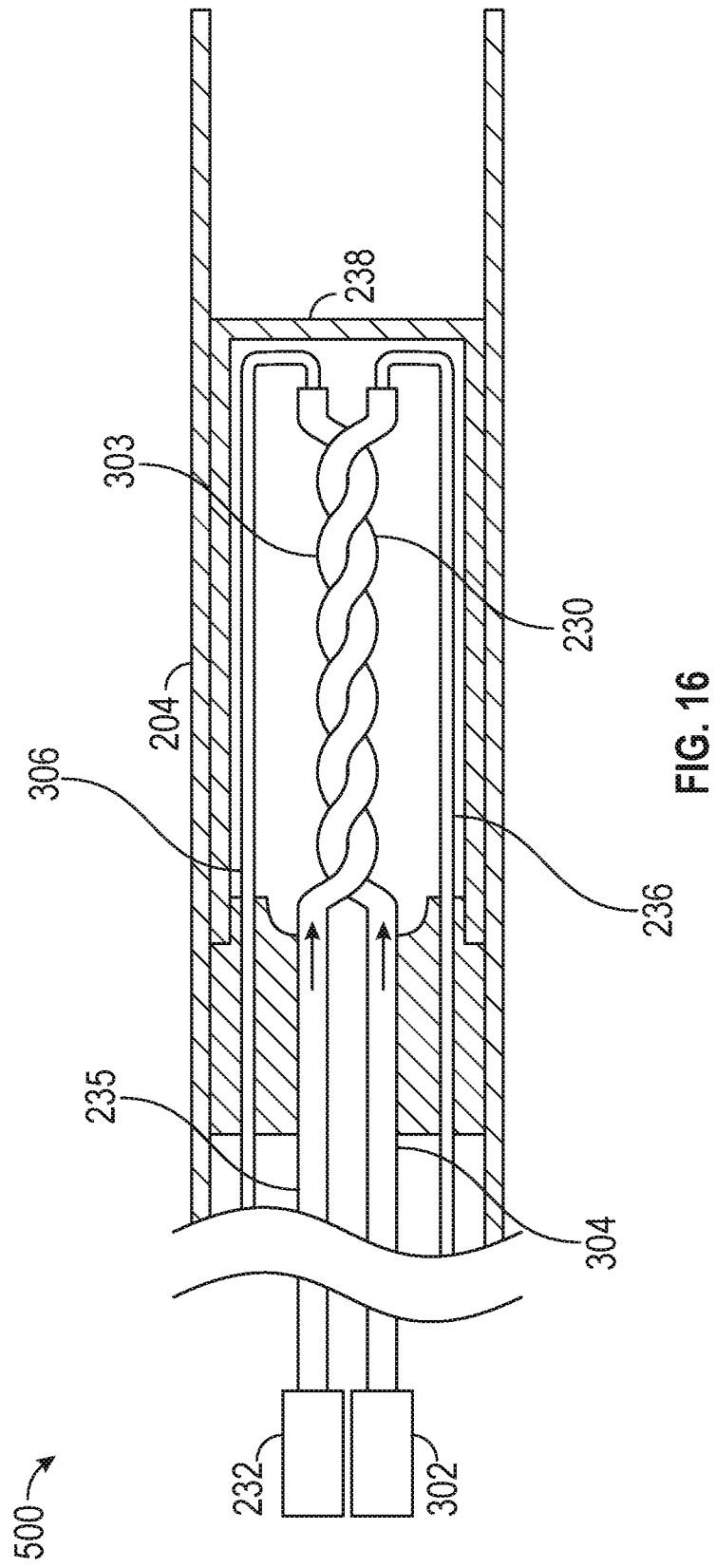
FIG. 16 illustrates a side-view of a portion of a therapy device, according to an example of the present disclosure.

While FIGS. 13 and 14 illustrate generating UV light externally, FIGS. 15 and 16 illustrate therapy devices 400 and 500, respectively, that provide UV ablation while generating the UV light in vivo. As seen in FIG. 15, the therapy device 400 includes the outer shaft 204, an optical light system 210, and a therapy light system 228. As discussed herein, the therapy light system 228 can generate UV light in vivo by activating a material (such as a gas) to emit a UV light that can treat tissue.

The optical light system 210 can provide a visual light that can be coupled to a camera such that the operator can view the target tissue. The optical light system 210 can be the same optical light system disclosed in FIGS. 13 and 14. Thus, the light conductor 224 can comprise a medium for transmitting light from light source 220 to light emitter 226. Light conductor 224 can be located within the light delivery shaft 222. Light conductor 224 can comprise a material suitable for transmitting waves of electromagnetic radiation at various wavelengths.

The device 400 can include a therapy light system 228 including a UV light source 230. The UV light source 230 is positioned within the shaft 204 and configured to extend from the shaft 204 during use. For example, the UV light source 230 can move relative to the shaft 204. The UV light source 230 is electrically connected to a power source via one or more electrical conductors.

The UV light source 230 can be, e.g., a bulb or UV light transparent tube that is configured to circulate a material that, when activated, can generate a UV light. In one example, the UV light source 230 can be in fluid communication with an inlet lumen 235 and an outlet lumen 236. The inlet lumen 235 is coupled to a material source 232 that can provide the material to be activated and apply UV light to treat target tissue. In one example, the material can be a gas that can be activated to produce an output of UV light that can ablate tissue. The material flowing through the therapy light system 228 can be activated within the UV light source 230 (e.g., a bulb). However, other configurations are possible.

In on example, the material source 232 can be switched from a first material to a second material to allow different materials to be easily used to apply different UV wavelengths to treat the tissue. For example, a first material used can provide a UV wavelength from 100-200 nm and a second material can be used to provide a UV wavelength form 200-400 nm. 200

The device 400 can include a UV transparent cover 238 that is coupled to a shaft (similar to shaft 19 in FIG. 3). The UV transparent cover 238 can protect the UV light source 230 and the surrounding anatomy in case of breakage of the UV light source 230.

FIG. 16 illustrates a therapy device 500 that can be used to apply two different UV wavelengths to treat target tissue. The therapy device 500 is similar to the therapy device 400 in FIG. 15, however, there are two light sources and the optical light system is not shown for simplicity. Instead of replacing the material source 232 in FIG. 15, FIG. 16 includes two therapy light sources (e.g., UV light sources 230, 303). Each UV light source 230, 303 is coupled to a material source 232, 302, respectively. For example, light source 230 is coupled to an inlet lumen 235 and an outlet lumen 236 to circulate the material contained within material source 232. Similarly, light source 303 is coupled to an inlet lumen 304 and an outlet lumen 306 to circulate the material contained in material source 302. As discussed herein, the materials contained within material sources 232, 302 can be any known materials that can produce a UV light that is sufficient to treat (ablate) target, tissue. As seen in FIG. 16. UV light sources 230, 303 are entwined helical tubes. However, other configurations are possible. This enables 360 degree coverage during the treatment without having to rotate or twist the device during use.

Figure 17:
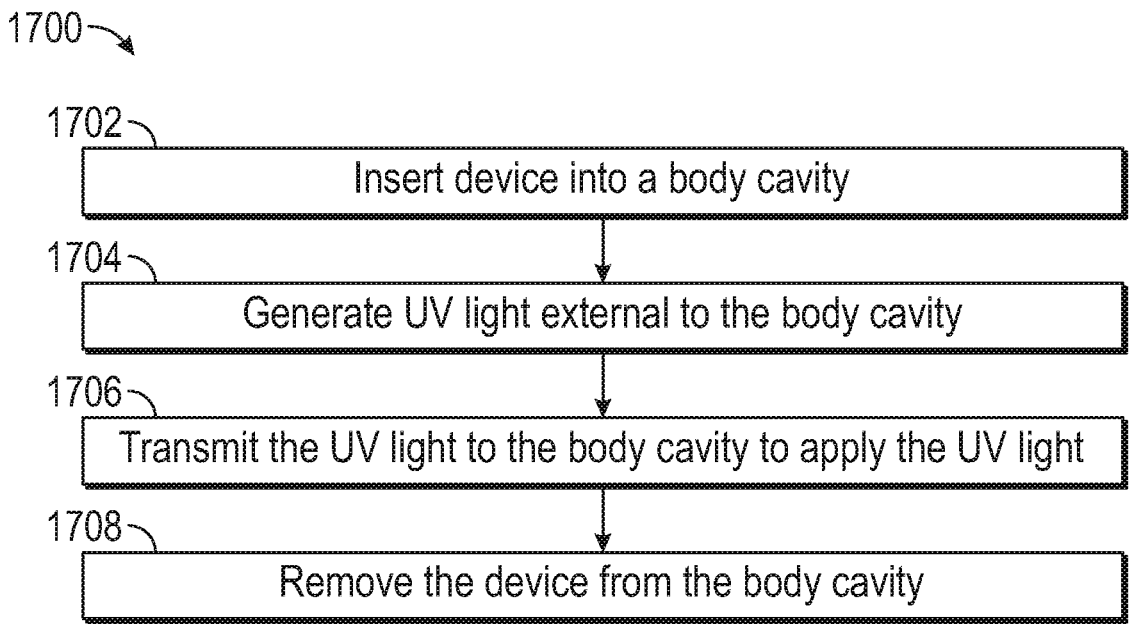
FIG. 17 is a schematic line diagram illustrating methods for providing UV ablation to a target tissue, according to one example of the present disclosure.

FIG. 17 is a line diagram illustrating method 1700 for providing UV ablation to a target tissue. Method 1700 can include applying UV light to a target tissue in a patient. The method 1700 can include inserting the device into a body cavity, at step 1702. That is, a distal portion of the outer shaft can be inserted into the patient. At step 1704, the method 1700 can include generating UV light external to the body cavity. For examples, devices 200 and 303 shown in FIGS. 13 and 14 can be used to generate the UV light external to the body cavity. After generating the UV light, the method 1700 can include transmitting the UV light to the body cavity to apply the UV light to the target tissue, at step 1706. For example, the generated UV light can be transmitted via a light conductor to the distal end of the therapy device such that the generated UV light can treat (e.g., ablate) the target tissue. After the UV light has been applied, the device can be removed from the body cavity, at step 1708.

Figure 18:
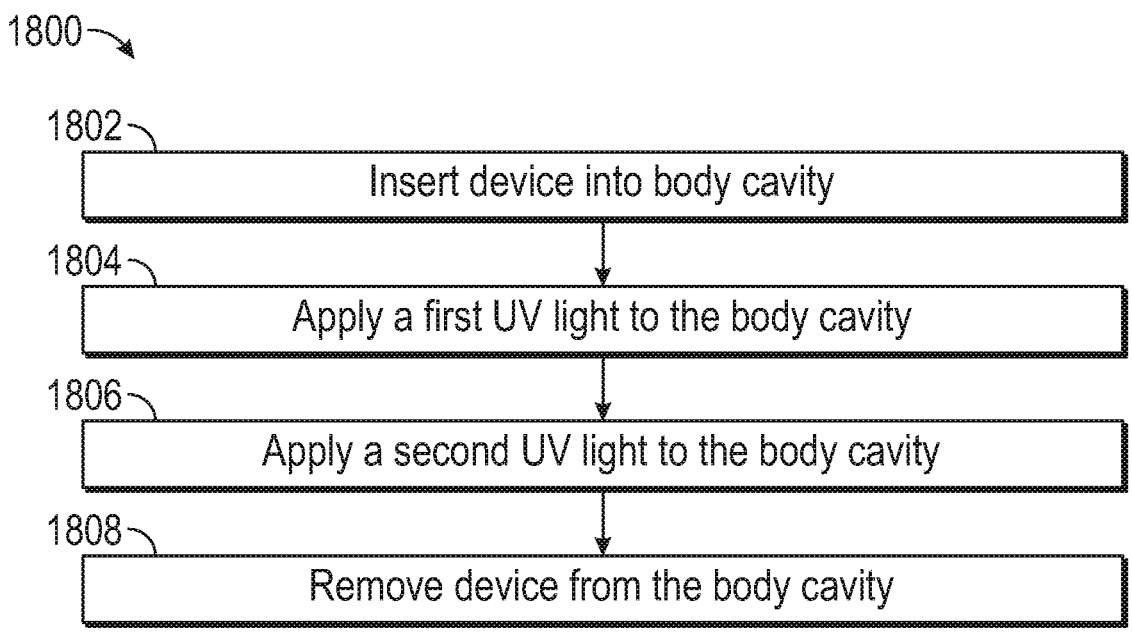
FIG. 18 is a schematic line diagram illustrating methods for providing UV ablation to a target tissue, according to one example of the present disclosure.

FIG. 18 is a line diagram illustrating method 1800 for providing UV ablation to a target tissue. Method 1800 can include applying UV light to a target tissue in a patient. The method 1800 can include inserting the device into a body cavity, at step 1802. That is, a distal portion of the outer shaft can be inserted into the patient. At step 1804, the method 1800 can include applying a first UV light to the body cavity. As discussed herein, a first UV light can be applied to the target tissue. After applying the first UV light (or simultaneously with the first UV light), a second UV light can be applied to the body cavity, at step 1806. In one example, a first UV light having a wavelength within 100 nm to 200 nm can be applied and subsequently (or simultaneously) a second UV light having a wavelength within 200 nm to 400 nm can be applied. After the first and second UV light has been applied, the device can be removed from the body cavity, at step 1808.

Figure 19:
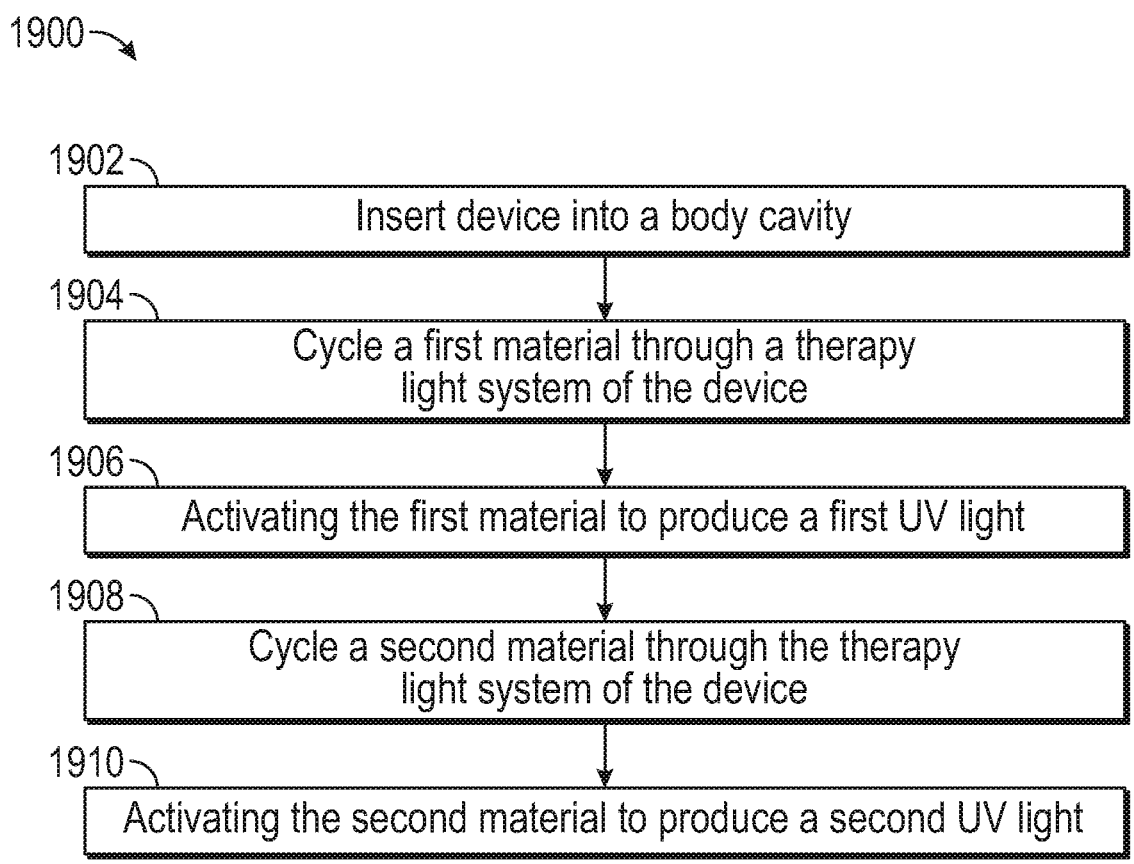
FIG. 19 is a schematic line diagram illustrating methods for providing UV ablation to a target tissue, according to one example of the present disclosure.

FIG. 19 is a line diagram illustrating method 1900 for providing UV ablation to a target tissue. Method 1900 can include applying UV light to a target tissue in a patient. The method 1900 can include inserting the device into a body cavity, at step 1902. That is, a distal portion of the outer shaft can be inserted into the patient. At step 1904, the method 1900 can include cycling a first material through the therapy light system of the device. For example, therapy devices in FIGS. 15 and 16 can be used to cycle a first material through a therapy light system. At step 1906, the first material can be activated to produce a first UV light. For example, the first material can be activated to produce a UV light having a wavelength within a range of 100 nm to 200 nm. At step 1908, the method 1900 can include cycling a second material through the therapy light system of the device. For example, therapy devices in FIGS. 15 and 16 can be used to cycle a first material through a therapy light system. For therapy device 400, the material source 232 can be switched such that the second material can be cycled through the device. For therapy device 500, a second material source 302 is included such that the second material can be cycled through the device. At step 1908, the second material can be activated to produce a second UV light. For example, the second material can be activated to produce a UV light having a wavelength within a range of 200 nm to 400 nm. After the UV light has been applied and an operator has determined that the target tissue has sufficiently been treated, the therapy device can be removed.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

VARIOUS EXAMPLES & NOTES

Each of these non-limiting examples can stand on its own, or can be combined in various permutations or combinations with one or more of the other examples.

Example 1 provides A therapy device for treating intra-uterine tissue, the therapy device including: a cannulated shaft extending from a proximal end to a distal end, the distal end having a distal opening; an ultra-violet (UV) light transparent distention member translatable within the cannulated shaft configured to extend from the distal opening and distend a patient's uterus; and a UV light source configured extend from the distal opening and apply an energy to the intra-uterine tissue.

In Example 2, the subject matter of Example 1 optionally includes where the UV light transparent distention member has a non-expanded position and an expanded position.

In Example 3, the subject matter of Example 2 optionally includes where, at the non-expanded position, the UV light transparent distention member is compressed within the cannulated shaft.

In Example 4, the subject matter of Example 2 optionally includes where, at the expanded position, the UV light transparent distention member is expanded and configured to distend the patient's uterus for treatment.

In Example 5, the subject matter of Example 2 optionally includes a handle coupled to the cannulated shaft, the handle including: a first actuator coupled to the UV light transparent distention member for transitioning the UV light transparent distention member between the non-expanded position and the expanded position.

In Example 6, the subject matter of Example 5 optionally includes where the handle further includes: a second actuator mechanically and electrically coupled to the UV light source configured to advance the UV light source from the cannulated shaft and deliver the energy for treating the intra-uterine tissue.

In Example 7, the subject matter of Example 6 optionally includes where the second actuator has an initial position, a first actuated position, and a second actuated position.

In Example 8, the subject matter of Example 7 optionally includes where, as the second actuator moves from the initial position to the first actuated position, the UV light source advances from the distal opening of the cannulated shaft.

In Example 9, the subject matter of Example 8 optionally includes where, as the second actuator moves from the first actuated position to the second actuated position, the UV light source generates the energy that is delivered to the intra-uterine tissue.

In Example 10, the subject matter of Examples 1-9 optionally includes where the UV light source is a flash lamp.

In Example 11, the subject matter of Example 10 optionally includes where the flash lamp is a xenon flash lamp.

In Example 12, the subject matter of Examples 1-11 optionally includes where the UV light source is a cold cathode UV bulb In Example 13, the subject matter of Examples 1-12 optionally includes where the therapy device does not include a fluid medium.

In Example 14, the subject matter of Example 13 optionally includes where the fluid medium includes at least one of gas, steam, and liquid.

Example 15 provides a method of treating a patient, the method comprising introducing a portion of a therapy device into a body cavity of a patient, the therapy device, including: a cannulated shaft extending from a proximal end to a distal end, the distal end having a distal opening; a UV light transparent distention member translatable within the cannulated shaft; and a UV light source; distending the body cavity by extending the UV light transparent distention member from the distal opening to distend the body cavity; and treating the body cavity by applying an energy generated by the UV light source to the body cavity.

In Example 16, the subject matter of Example 15 optionally provides where the UV light transparent distention member has a non-expanded position and an expanded position.

In Example 17, the subject matter of Example 16 optionally includes where extending the UV light transparent distention member from the distal opening transitions the UV light transparent distention member from the non-expanded position to the expanded position.

In Example 18, the subject matter of Example 16 optionally includes where the therapy device further includes: a handle coupled to the cannulated shaft, the handle including: a first actuator coupled to the UV light transparent distention member for actuating the UV light transparent distention member between the non-expanded position and the expanded position; and a second actuator mechanically and electrically coupled to the UV light source configured to advance the UV light source from the cannulated shaft and deliver the energy for treating the body cavity.

In Example 19, the subject matter of Example 18 optionally includes where distending the body cavity includes activating the first actuator to move the UV light transparent distention member from the cannulated shaft thereby transitioning the UV light transparent distention member from the non-expanded position to the expanded position.

In Example 20, the subject matter of Example 18 optionally includes where the second actuator has an initial position, a first actuated position, and a second actuated position.

In Example 21, the subject matter of Example 20 optionally includes where treating the body cavity includes: moving the second actuator from the initial position to the first actuated position to advance the UV light source from the distal opening of the cannulated shaft; and moving the second actuator from the first actuated position to the second actuated position to generate the energy and treat the body cavity.

Example 22 provides a device for visualizing internal tissue of a body cavity, the device comprising: a cannulated shaft extending from a proximal end to a distal end, the distal end having a distal opening; a distention member translatable within the cannulated shaft configured to distend the body cavity; a light source configured extend from the distal opening and illuminate the internal tissue of the body cavity; and an image visualization structure configured to visualize the internal tissue of the body cavity to a user.

In Example 23, the subject matter of Example 22 optionally includes where the distention member is formed from a light transparent material.

In Example 24, the subject matter of Example 22 optionally includes where the distention member has a non-expanded position and an expanded position.

In Example 25, the subject matter of Example 24 optionally includes where, at the non-expanded position, the distention member is compressed within the cannulated shaft.

In Example 26, the subject matter of Example 25 optionally includes where, at the expanded position, the distention member is expanded and configured to distend the patient's body cavity.

In Example 27, the subject matter of Examples 22 optionally includes where further including: a handle coupled to the cannulated shaft, the handle including: a first actuator coupled to the distention member for actuating the distention member between the non-expanded position and the expanded position In Example 28, the subject matter of Examples 27 optionally includes wherein the handle further includes: a second actuator mechanically and electrically coupled to the light source configured to advance the light source from the cannulated shaft and deliver power to the light source.

In Example 29, the subject matter of Example 27 optionally includes where the second actuator is further mechanically coupled to the image visualization structure configured to advance the image visualization structure from the cannulated shaft.

In Example 30, the subject matter of Example 29 optionally includes where the light source and image visualization structure have a predefined space between the two.

In Example 31, the subject matter of Example 22 optionally includes where the light source is a light emitting diode (LED) light.

In Example 32, the subject matter of Example 22 optionally includes where the image visualization structure is at least one of a charge-coupled device (CCD), a complementary metal-oxide-semiconductor (CMOS) chip, and a lens.

In Example 33, the subject matter of Example 22 optionally includes where the image visualization structure and the light source are positioned along a longitudinal axis of the cannulated shaft.

In Example 34, the subject matter of Example 32 optionally includes the visualization structure is positioned distal relative to the light source.

In Example 35, the subject matter of Example 32 optionally includes where the visualization structure is positioned proximal relative to the light source.

In Example 36, the subject matter of Example 32 optionally includes where the light source is coaxial with the visualization structure.

In Example 37, the subject matter of Example 32 optionally includes where the light source and the visualization structure are concentric with each other.

In Example 38, the subject matter of Example 22 optionally includes where at least one of the light source and the visualization structure are offset from a longitudinal axis of the cannulated shaft.

In Example 39, the subject matter of Examples 22 optionally includes a monitor configured to receive and display video signals from the image visualization structure.

Example 40 provides a method of visualizing internal tissue of a body cavity, the method comprising: introducing a portion of a device into a body cavity of a patient, the device, including: a cannulated shaft extending from a proximal end to a distal end, the distal end having a distal opening; a distention member translatable within the cannulated shaft configured to distend the body cavity; a light source configured extend from the distal opening and illuminate the internal tissue of the body cavity; and an image visualization structure configured to visualize the internal tissue of the body cavity to a user; distending the body cavity by extending the distention member from the distal opening to distend the body cavity; and illuminating the body cavity with light generated from the light source.

In Example 41, the subject matter of Example 40 optionally includes where the distention member has a non-expanded position and an expanded position.

In Example 42, the subject matter of Example 41 optionally includes where extending the distention member from the distal opening expands the distention member from the non-expanded position to the expanded position.

In Example 43, the subject matter of Example 42 optionally includes where the visualization structure is positioned proximal relative to the light source.

Example 44 provides

In Example 45, the subject matter of Example 44 optionally includes where the visualization structure is positioned proximal relative to the light source.

In Example 46, the subject matter of Example 44 optionally includes where the visualization structure is positioned proximal relative to the light source.

In Example 47, the subject matter of Example 44 optionally includes where the visualization structure is positioned proximal relative to the light source.

In Example 48, the subject matter of Example 4 optionally includes where the at least one working shaft includes a plurality of working shafts.

Example 49 provides a therapy device for treating intra-uterine tissue, the therapy device including: a cannulated shaft extending from a proximal end to a distal end, the distal end having a distal opening; and a therapy light system configured to apply UV light to treat the intra-uterine tissue, wherein the therapy light system, includes: a light source configured to generate a wavelength within the UV band; a light conductor coupled to the light source; and a light emitter connected to the light conductor to emit the UV light from the light conductor toward the intra-uterine tissue.

In Example 50, the subject matter of Example 49 optionally includes where the UV light is generated external to the patient and transmitted to the light emitter via the light conductor Example 51 provides a method of applying UV light to an intra-uterine tissue, the method includes: introducing a portion of a therapy device into a body cavity of a patient, the therapy device, including: a cannulated shaft extending from a proximal end to a distal end, the distal end having a distal opening; a therapy light system including: a light source configured to generate a wavelength within the UV band; a light conductor coupled to the light source; and a light emitter connected to the light conductor to emit the UV light from the light conductor toward the intra-uterine tissue; generating the UV light external to the body cavity of the patient; and transmitting the UV light via a light conductor to a light emitter positioned within the body cavity to apply the UV light to the body cavity.

Example 52 provides a therapy device for treating intra-uterine tissue, the therapy device including: a cannulated shaft extending from a proximal end to a distal end, the distal end having a distal opening; and a therapy light system configured to apply UV light to treat the intra-uterine tissue, wherein the therapy light system, includes: a first UV light source configured to generate a first UV light having a wavelength within 100 nanometers (nm) to 200 nm; a light conductor reversibly coupled to the first light source; a light emitter connected to the light conductor to emit the first UV light from the light conductor toward the intra-uterine tissue; and a second UV light source reversibly coupled to the light conductor, the second UV light source configured to generate a second UV light having a wavelength within 200 nm to 400 nm.

Example 53 provides a method of apply UV light to an intra-uterine tissue, the method includes: introducing a portion of a therapy device into a body cavity of a patient, the therapy device, including: a cannulated shaft extending from a proximal end to a distal end, the distal end having a distal opening; a therapy light system including: a first UV light source configured to generate a first UV light with a wavelength within 100 nm to 200 nm; a second UV light source configured to generate a first UV light with a wavelength within 200 nm to 400 nm; generating the first UV light external to the body cavity of the patient; transmitting the first UV light to the body cavity to apply the UV light to the body cavity; generating the second UV light external to the body cavity of the patient; and transmitting the second UV light to the body cavity to apply the UV light to the body cavity.

Example 54 provides a method of apply UV light to an intra-uterine tissue, the method includes: introducing a portion of a therapy device into a body cavity of a patient, the therapy device, including: a cannulated shaft extending from a proximal end to a distal end, the distal end having a distal opening; a therapy light system including: a first UV light source configured to generate a first UV light with a wavelength within 100 nm to 200 nm; a second UV light source configured to generate a first UV light with a wavelength within 200 nm to 400 nm; generating the first UV light; applying the first UV light to the intra-uterine tissue; generating the second UV light; and applying the second UV light to the intra-uterine tissue.

In Example 55, includes the combination of any one of the Examples 1-54.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. A therapy device for treating intra-uterine tissue, the therapy device including:
   a cannulated shaft extending from a proximal end to a distal end, the distal end having a distal opening;
   a UV light transparent distention member translatable within the cannulated shaft configured to extend from the distal opening and distend a patient's uterus; and
   a therapy light system configured to apply ultra-violet (UV) light to treat the intra-uterine tissue, wherein the therapy light system includes:
      a first UV light source coupled with a first material source containing a first material, the first material configured to produce a first UV light with a first wavelength; and
      a second UV light source coupled with a second material source containing a second material, the second material configured to produce a second UV light with a second wavelength different from the first wavelength of the first UV light;
wherein the first material is configured to be circulated through the first UV light source;
wherein the second material is configured to be circulated through the second UV light source.

2. The therapy device of claim 1, wherein the first wavelength is within 100 nanometers (nm) to 200 nm.

3. The therapy device of claim 2, wherein the second wavelength is within 200 nanometers (nm) to 400 nm.

4. The therapy device of claim 1, wherein the therapy light system further includes:
at least one first inlet lumen and at least one second inlet lumen configured to be reversibly coupled to at least one of the first UV light source and the second UV light source;
the first UV light source includes at least one first bulb configured to emit the first UV light when the first UV light source is coupled with a proximal end of the at least one first inlet lumen and the at least one first bulb is coupled to a distal end of the at least one first inlet lumen; and
the second UV light source includes at least one second bulb configured to emit the second UV light when the second UV light source is coupled with a proximal end of the at least one second inlet lumen and the at least one second bulb is coupled to a distal end of the at least one second inlet lumen.

5. The therapy device of claim 1, wherein the therapy light system further includes:
a proximal end of a first inlet lumen coupled to the first UV light source; and
a first bulb connected to a distal end of the first inlet lumen the first bulb configured to emit the first UV light.

6. The therapy device of claim 5, wherein the therapy light system further includes:
a proximal end of a second inlet lumen coupled to the second UV light source; and
a second bulb connected to a distal end of the second inlet lumen, the second bulb configured to emit the second UV light.

7. The therapy device of claim 1, wherein the UV light transparent distention member has a non-expanded position and an expanded position.

8. The therapy device of claim 7, wherein, at the non-expanded position, the UV light transparent distention member is compressed within the cannulated shaft, and wherein, at the expanded position, the UV light transparent distention member is expanded and configured to distend the patient's uterus for treatment.

9. The therapy device of claim 1, wherein at least one of the first UV light source and the second UV light source is a flash lamp.

10. The therapy device of claim 9, wherein the flash lamp is a xenon flash lamp.

11. The therapy device of claim 1, wherein at least one of the first UV light source and the second UV light source is a cold cathode UV bulb.

12. A therapy device for treating intra-uterine tissue, the therapy device including:
a cannulated shaft extending from a proximal end to a distal end, the distal end having a distal opening;
a therapy light system configured to apply ultra-violet (UV) light to treat the intra-uterine tissue, the therapy light system, includes:
a first UV light source configured to circulate a first material from a first material source, the first material configured to generate a first UV light with a first wavelength; and
a second UV light source configured to circulate a second material from a second material source, the second material configured to generate a second UV light with a second wavelength different from the first wavelength of the first UV light;
wherein the first UV light source and the second UV light source are each configured to extend from the cannulated shaft;
a UV light transparent distention member translatable within the cannulated shaft configured to extend from the distal opening and distend a patient's uterus;
a light source configured extend from the distal opening and illuminate internal tissue of a body cavity; and
an image visualization structure configured to visualize the internal tissue of the body cavity to a user.

13. The therapy device of claim 12, wherein the first wavelength is within 100 nanometers (nm) to 200 nm.

14. The therapy device of claim 13, wherein the second wavelength is within 200 nanometers (nm) to 400 nm.

15. The therapy device of claim 1 wherein at least one of the first UV light source and the second UV light source are located within the cannulated shaft.

16. The therapy device of claim 15, wherein at least one of the first UV light source and the second UV light source are configured to extend from the cannulated shaft;
wherein at least one of the first UV light source and the second UV light source is configured to move relative to the cannulated shaft.

17. The therapy device of claim 12, wherein the first UV light source and the second UV light source are entwined in a helical configuration.

18. The therapy device of claim 1, wherein at least a portion of at least one of the first UV light source and the second UV light source is positioned within the cannulated shaft and at least a portion of the therapy light system is configured to extend from the cannulated shaft.

19. The therapy device of claim 1, wherein at least one of the first UV light source and second UV light source has an inlet lumen and an outlet lumen housed within the cannulated shaft.

* * * * *